(12) United States Patent
Kumar et al.

(10) Patent No.: US 10,603,359 B2
(45) Date of Patent: Mar. 31, 2020

(54) METHODS AND COMPOSITIONS USING GDF15 POLYPEPTIDES FOR INCREASING RED BLOOD CELLS

(71) Applicant: Acceleron Pharma Inc., Cambridge, MA (US)

(72) Inventors: Ravindra Kumar, Acton, MA (US); Naga Venkata Sai Rajasekhar Suragani, Wrentham, MA (US)

(73) Assignee: ACCELERON PHARMA INC., Cambridge, MA (US)

( * ) Notice: Subject to any disclaimer, the term of this patent is extended or adjusted under 35 U.S.C. 154(b) by 0 days.

(21) Appl. No.: 15/523,025

(22) PCT Filed: Oct. 29, 2015

(86) PCT No.: PCT/US2015/058116
§ 371 (c)(1),
(2) Date: Apr. 28, 2017

(87) PCT Pub. No.: WO2016/069925
PCT Pub. Date: May 6, 2016

(65) Prior Publication Data
US 2018/0207236 A1    Jul. 26, 2018

Related U.S. Application Data

(60) Provisional application No. 62/072,889, filed on Oct. 30, 2014.

(51) Int. Cl.
```
A61K 38/18      (2006.01)
C07K 14/475     (2006.01)
A61P 7/06       (2006.01)
```

(52) U.S. Cl.
CPC .......... *A61K 38/18* (2013.01); *A61K 38/1816* (2013.01); *A61K 38/1841* (2013.01); *A61P 7/06* (2018.01); *C07K 14/475* (2013.01)

(58) Field of Classification Search
None
See application file for complete search history.

(56) References Cited

U.S. PATENT DOCUMENTS

| | | |
|---|---|---|
| 4,965,251 A | 10/1990 | Stamatoyannopoulos |
| 7,988,973 B2 | 8/2011 | Sherman |
| 8,058,229 B2 | 11/2011 | Seehra et al. |
| 8,216,997 B2 | 7/2012 | Seehra et al. |
| 9,809,637 B2 | 11/2017 | Kumar et al. |
| 2011/0038831 A1 | 2/2011 | Seehra et al. |
| 2013/0330343 A1* | 12/2013 | Mueller ................ C07K 16/18 424/135.1 |
| 2014/0194489 A1* | 7/2014 | Bumcrot ............. C12Y 304/21 514/44 A |
| 2014/0213511 A1 | 7/2014 | Matern et al. |
| 2014/0315752 A1 | 10/2014 | Anderberg et al. |
| 2015/0045199 A1 | 2/2015 | Thorwid et al. |
| 2015/0337034 A1* | 11/2015 | Schurpf ............... C07K 14/495 530/387.3 |
| 2016/0046690 A1 | 2/2016 | Kumar et al. |
| 2017/0024077 A1 | 1/2017 | Lin et al. |
| 2017/0137506 A1* | 5/2017 | Gyuris .................. C07K 16/22 |
| 2017/0299608 A1* | 10/2017 | Hsu .................... G01N 33/6854 |

FOREIGN PATENT DOCUMENTS

| | | |
|---|---|---|
| WO | WO-2000/011168 A2 | 3/2000 |
| WO | WO-2011/020045 A1 | 2/2011 |
| WO | WO-2013/113008 A1 | 8/2013 |
| WO | WO-2014/100689 A1 | 6/2014 |
| WO | WO-2014/120619 A2 | 8/2014 |

OTHER PUBLICATIONS

Tokuriki et al., 2009, Curr. Opin. Struc. Biol. 19:596-604.*
Bhattacharya et al., 2017, PLoS ONE 12(3): e0171355, https://doi.org/10.1371/journal.pone.0171355.*
Adamson, "Iron Deficiency and Other Hypoproliferative Anemias," Section 2 Hematopoietic Disorders, Harrison's Principles of Internal Medicine, 17th Edition, McGraw Hill, New York: 628-634.
Aizawa et al., "Ineffective Erythropoiesis in the Spleen of a Patient With Pyruvate Kinase Deficiency," American Journal of Hematology, vol. 74: 68-72 (2003).
Ballas et al., "Red Blood Cell Changes During the Evolution of the Sickle Cell Painful Crisis," Blood, vol. 79(8): 2154-2163 (1992).
Bron et al., "Biological Basis of Anemia," Seminars in Oncology, vol. 28(2) Suppl 8: 1-6 (2001).
Bunn, "Drug-Induced Autoimmune Red-Cell Aplasia," The New England Journal of Medicine, vol. 346(7): 522-523 (2002).
Cao et al., "Recent advances in β-thalassemias," Pediatric Reports, vol. 3:e17: 65-78 (2011).
Cui et al., "Serum iron metabolism and erythropoiesis in patients with myelodysplastic syndrome anot receiving RBC transusions," Leuk Res., vol. 38(5): 545-550 (2014).
Delanty et al., "Erythropoietin-associated hypertensive posterior leukoencephalopathy," Neurology, vol. 49: 686-689 (1997).
Demetri et al., "Quality-of-Life Benefit in Chemotherapy Patients Treated With Epoetin Alfa Is Independent of Disease Response or Tumor Type: Results From a Prospective Community Oncology Study," Journal of Clinical Oncology, vol. 16(10): 3412-3425 (1998).
Di Matteo et al., "Bone and Maxillofacial Abnormalities in Thalassemia: A Review of the Literature," Journal of Biological Regulators and Homeostatic Agents, vol. 22(4): 211-216 (2008).
Eaton et al., "Sickle Cell Hemoglobin Polymerization," Advances in Protein Chemistry, vol. 40: 63-279 (1990).

(Continued)

*Primary Examiner* — Elizabeth C. Kemmerer
(74) *Attorney, Agent, or Firm* — White & Case LLP

(57) ABSTRACT

In certain aspects, the present invention provides compositions and methods for increasing red blood cell and/or hemoglobin levels in vertebrates, including rodents and primates, and particularly in humans.

12 Claims, 5 Drawing Sheets
(5 of 5 Drawing Sheet(s) Filed in Color)
Specification includes a Sequence Listing.

(56) References Cited

OTHER PUBLICATIONS

Eschbach et al., "Correction of the Anemia of End-Stage Renal Disease with Recombinant Human Erythropoietin," The New England Journal of Medicine, vol. 316(2): 73-78 (1987).
Esposito et al., "Labile plasma iron in iron overload: redox activity and susceptibility to chelation," Blood, vol. 102(7): 2670-2677 (2003).
Estey, "Current challenges in therapy of myelodysplastic syndromes," Current Opinion in Hematology, vol. 10: 60-67 (2003).
Gafter et al., "Anemia of uremia is associated with reduced in vitro cytokine secretion: Immunopotentiating activity of red blood cells," Kidney International, vol. 45: 224-231 (1994).
Galanello et al., "Beta-thalassemia," Orphanet Journal of Rare Diseases, vol. 5(11): 1-15 (2010).
Galanello et al., "Combined iron chelation therapy," Annals of the New York Academy of Sciences, vol. 1202: 79-86 (2010).
Ganz, "Molecular Control of Iron Transport," Journal of the American Society of Nephrology, vol. 18: 394-400 (2007).
Gardenghi et al., "Hepcidin as a therapeutic tool to limit iron overload and improve anemia in β-thalassemic mice," The Journal of Clinical Investigation, vol. 120(12): 4466-4477 (2010).
Glaspy et al., "Impact of Therapy With Epoetin Alfa on Clinical Outcomes in Patients With Nonmyeloid Malignancies During Cancer Chemotherapy in Community Oncology Practice," Journal of Clinical Oncology, vol. 15(3): 1218-1234 (1997).
Glaspy et al., "Erythropoietin in Cancer Patients," Annual Reviews in Medicine, vol. 60: 181-192 (2009).
Groopman et al., "Chemotherapy-Induced Anemia in Adults: Incidence and Treatment," Journal of the National Cancer Institute, vol. 91(19): 1616-1634 (1999).
Haidar et al., "Bone disease and skeletal complications in patients with β thalassemia major," Bone, vol. 48: 425-432 (2011).
Hershko, "Oral iron chelators: new opportunities and new dilemmas," haematologica/the hematology journal, vol. 91(10): 1307-1312 (2006).
Horl et al., "European Best Practice Guidelines 14-16 Inadequate response to epoetin," Nephrology Dialysis Transplantation, vol. 15(Suppl 4): 43-50 (2000).
Horl et al., "European Best Practice Guidelines 17-18 Adverse effects," Nephrology Dialysis Transplantation, vol. 15(Suppl 4): 51-56 (2000).
Jacobs et al., "European Best Practice Guidelines 5 Target haemoglobin," Nephrology Dialysis Transplantation, vol. 15(Suppl 4): 15-19 (2000).
Jelkmann et al., "The erythropoietin receptor in normal and cancer tissues," Critical Reviews in Oncology/Hematology, vol. 67: 39-61 (2008).
Kalinowski et al., "The Evolution of Iron Chelators for the Treatment of Iron Overload Disease and Cancer," Pharmacological Reviews, vol. 57(4): 547-583 (2005).
Kassim et al., "Sickle Cell Disease, Vasculopathy, and Therapeutics," Annual Reviews in Medicine, vol. 64: 451-466 (2013).
Krapf et al., "Arterial Hypertension Induced by Erythropoietin and Erythropoiesis-Stimulating Agents (ESA)," Clinical Journal of the American Society of Nephrology, vol. 4: 470-480 (2009).
Lekawanvijit et al., "Iron overload thalassemic cardiomyopathy: Iron status assessment and mechanisms of mechanical and electrical disturbance due to iron toxicity," Canadian Journal of Cardiology, vol. 25(4): 213-218 (2009).
Levin, "Prevalent Left Ventricular Hypertrophy in the Predialysis Population: Identifying Opportunities for Intervention," American Journal of Kidney Diseases, vol. 27(3): 347-354 (1996).
Nissenson, "Epotin and Cognitive Function," American Journal of Kidney Diseases, vol. 20(1) Suppl 1:21-24 (1992).
Massague, "How Cells Read TGF-β Signals," Nature Reviews Molecular Cell Biology, vol. 1: 169-178 (2000).
Musallam et al., "Iron overload in non-transfusion-dependent thalassemia: a clinical perspective," Blood Reviews, vol. 26S: S16-S19 (2012).

Musallam et al., "β-Thalassemia Intermedia: A Clinical Perspective," Cold Spring Harbor Perspectives in Medicine, vol. 2:a013482: 1-15 (2012).
Nemeth, "Targeting the Hepcidin-Ferroportin Axis in the Diagnosis and Treatment of Anemias," Advances in Hematology, vol. 2010: 1-9 (2010).
Paulson et al., "Stress erythropoiesis: new signals and new stress progenitor cells," Current Opinion in Hematology, vol. 18(3): 139-145 (2011).
Pippard et al., "Iron Absorption and Loading in β-Thalassaemia Intermedia," The Lancet: 819-821 (1979).
Porter et al., "Mechanisms of plasma non-transferrin bound iron generation: insights from comparing transfused diamond blackfan anaemia with sickle cell and thalassaemia patients," Br. Journal Haematol., vol. 167(5): 692-696 (2014).
Ramos et al., "Enhanced erythropoiesis in Hfe-KO mice indicates a role for Hfe in the modulation of erythroid iron homeostasis," Blood, vol. 117(4): 1379-1389 (2011).
Revicki et al., "Health-Related Quality of Life Associated With Recombinant Human Erythropoietin Therapy for Predialysis Chronic Renal Disease Patients," American Journal of Kidney Diseases, vol. 25(4): 548-554 (1995).
Ricketts et al., "Ferrokinetics: Methods and Interpretation," Clinical Nuclear Medicine, vol. 3: 159-164 (1978).
Rund et al., "β-Thalassemia," The New England Journal of Medicine, vol. 353: 1135-1146 (2005).
Schrier, "Pathophysiology of thalassemia," Current Opinion in Hematology, vol. 9: 123-126 (2002).
Setty et al., "Role of erythrocyte phosphatidylserine in sickle red cell-endothelial adhesion," Blood, vol. 99(5): 1564-1571 (2002).
Singbartl, "Adverse events of erythropoietin in long-term and in acute/short-term treatment," The Clinical Investigator, vol. 72(6): S36-S43 (1994).
Steinberg, "Management of Sickle Cell Disease," The New England Journal of Medicine, vol. 340(13): 1021-1030 (1999).
Tanno et al., "Growth differentiation factor 15 in crythroid health and desease," Current Opin Hematol., vol. 17(3): 184-190 (2010).
Tanno et al., "High levels of GDF15 in thalassemia suppress expression of the iron regulatory protein hepcidin," Nature Medicine, vol. 13(9): 1096-1101 (2007).
Tanno et al., "Iron Loading and Overloading due to Ineffective Erythropoiesis," Advances in Hematology, 2010:358283: 7 pages (2010).
Vaulont et al., "Erythroblasts-derived GDF15 supresses hepcidin in thalassemia," Med Sci (Paris) vol. 24(2): 139-141 (2008).
Vichinsky, "Changing Patterns of Thalassemia Worldwide," Annals of the New York Academy of Sciences, vol. 1054: 18-24 (2005).
Weatherall et al., "Red Cells I: inherited anaemias," The Lancet, vol. 355: 1169-1175 (2000).
Abandoned U.S. Appl. No. 12/286,381.
Issued U.S. Pat. No. 8007809 (U.S. Appl. No. 12/286,333).
Pending U.S. Appl. No. 13/189,353.
Abandoned U.S. Appl. No. 14/689,477.
Pending U.S. Appl. No. 15/714,015.
Pending U.S. Appl. No. 15/343,757.
Issued U.S. Pat. No. 9505813 (U.S. Appl. No. 13/750,249).
Pending U.S. Appl. No. 14/664,651.
Jelkmann, Wolfgang, "Developments in the therapeutic use of erythropoiesis stimulating agents," British Journal of Haematology, vol. 141: 287-297 (2008).
Kim and Nemeth, "New Insights into iron regulation and erythropoiesis," Curr Opin Hematol., vol. 22(3): 199-205 (2015).
Lenox et al., "Extramedullary erythropoiesis in the adult liver requires BMP4/Smad5 dependent signaling," Exp. Hematol., vol. 37(5): 549-558 (2009).
Chambers, David J., "Mechanism of Iron Regulation by Stress Cytokine GDF15", Esmolol Cardioplegia: the Nippon Medical School, vol. 7(1): p. 39 (2011) (English translation).

\* cited by examiner

```
             *    * ********* * ** * ****** *******   *   ** * **    * ** ***
mGDF15   AHPRDSCPLGPGRCCHLETVQATLEDLGWSDWVLSPRQLQLSMCVGECPHLYRSANTHAQ
hGDF15   ARNGDHCPLGPGRCCRLHTVRASLEDLGWADWVLSPREVQVTMCIGACPSQFRAANMHAQ

**   ** * ** ******** ** * **     ** **********  *   ***
mGDF15   IKARLHGLQPDKVPAPCCVPSSYTPVVLMHRTDSGVSLQTYDDLVARGCHCA
hGDF15   IKTSLHRLKPDTVPAPCCVPASYNPMVLIQKTDTGVSLQTYDDLLAKDCHCI
```

FIGURE 1

SEQUENCE LISTING

```
<160> NUMBER OF SEQ ID NOS: 15

<210> SEQ ID NO 1
<211> LENGTH: 308
<212> TYPE: PRT
<213> ORGANISM: Homo sapiens

<400> SEQUENCE: 1

Met Pro Gly Gln Glu Leu Arg Thr Val Asn Gly Ser Gln Met Leu Leu
1               5                   10                  15

Val Leu Leu Val Leu Ser Trp Leu Pro His Gly Gly Ala Leu Ser Leu
                20                  25                  30

Ala Glu Ala Ser Arg Ala Ser Phe Pro Gly Pro Ser Glu Leu His Ser
            35                  40                  45

Glu Asp Ser Arg Phe Arg Glu Leu Arg Lys Arg Tyr Glu Asp Leu Leu
        50                  55                  60

Thr Arg Leu Arg Ala Asn Gln Ser Trp Glu Asp Ser Asn Thr Asp Leu
65                  70                  75                  80

Val Pro Ala Pro Ala Val Arg Ile Leu Thr Pro Glu Val Arg Leu Gly
                85                  90                  95

Ser Gly Gly His Leu His Leu Arg Ile Ser Arg Ala Ala Leu Pro Glu
            100                 105                 110

Gly Leu Pro Glu Ala Ser Arg Leu His Arg Ala Leu Phe Arg Leu Ser
        115                 120                 125

Pro Thr Ala Ser Arg Ser Trp Asp Val Thr Arg Pro Leu Arg Arg Gln
    130                 135                 140

Leu Ser Leu Ala Arg Pro Gln Ala Pro Ala Leu His Leu Arg Leu Ser
145                 150                 155                 160

Pro Pro Pro Ser Gln Ser Asp Gln Leu Leu Ala Glu Ser Ser Ser Ala
                165                 170                 175
```

Arg Pro Gln Leu Glu Leu His Leu Arg Pro Gln Ala Ala Arg Gly Arg
            180                 185                 190

Arg Arg Ala Arg Ala Arg Asn Gly Asp His Cys Pro Leu Gly Pro Gly
            195                 200                 205

Arg Cys Cys Arg Leu His Thr Val Arg Ala Ser Leu Glu Asp Leu Gly
            210                 215                 220

Trp Ala Asp Trp Val Leu Ser Pro Arg Glu Val Gln Val Thr Met Cys
225                 230                 235                 240

Ile Gly Ala Cys Pro Ser Gln Phe Arg Ala Ala Asn Met His Ala Gln
            245                 250                 255

Ile Lys Thr Ser Leu His Arg Leu Lys Pro Asp Thr Val Pro Ala Pro
            260                 265                 270

Cys Cys Val Pro Ala Ser Tyr Asn Pro Met Val Leu Ile Gln Lys Thr
            275                 280                 285

Asp Thr Gly Val Ser Leu Gln Thr Tyr Asp Asp Leu Leu Ala Lys Asp
            290                 295                 300

Cys His Cys Ile
305

<210> SEQ ID NO 2
<211> LENGTH: 279
<212> TYPE: PRT
<213> ORGANISM: Homo sapiens

<400> SEQUENCE: 2

Leu Ser Leu Ala Glu Ala Ser Arg Ala Ser Phe Pro Gly Pro Ser Glu
1               5                   10                  15

Leu His Ser Glu Asp Ser Arg Phe Arg Glu Leu Arg Lys Arg Tyr Glu
            20                  25                  30

Asp Leu Leu Thr Arg Leu Arg Ala Asn Gln Ser Trp Glu Asp Ser Asn
            35                  40                  45

Thr Asp Leu Val Pro Ala Pro Ala Val Arg Ile Leu Thr Pro Glu Val
        50                  55                  60

Arg Leu Gly Ser Gly Gly His Leu His Leu Arg Ile Ser Arg Ala Ala
65                  70                  75                  80

Leu Pro Glu Gly Leu Pro Glu Ala Ser Arg Leu His Arg Ala Leu Phe
            85                  90                  95

Arg Leu Ser Pro Thr Ala Ser Arg Ser Trp Asp Val Thr Arg Pro Leu
            100                 105                 110

Arg Arg Gln Leu Ser Leu Ala Arg Pro Gln Ala Pro Ala Leu His Leu
            115                 120                 125

Arg Leu Ser Pro Pro Pro Ser Gln Ser Asp Gln Leu Leu Ala Glu Ser
            130                 135                 140

Ser Ser Ala Arg Pro Gln Leu Glu Leu His Leu Arg Pro Gln Ala Ala
145                 150                 155                 160

Arg Gly Arg Arg Arg Ala Arg Ala Arg Asn Gly Asp His Cys Pro Leu
            165                 170                 175

Gly Pro Gly Arg Cys Cys Arg Leu His Thr Val Arg Ala Ser Leu Glu
            180                 185                 190

Asp Leu Gly Trp Ala Asp Trp Val Leu Ser Pro Arg Glu Val Gln Val
            195                 200                 205

Thr Met Cys Ile Gly Ala Cys Pro Ser Gln Phe Arg Ala Ala Asn Met
            210                 215                 220

His Ala Gln Ile Lys Thr Ser Leu His Arg Leu Lys Pro Asp Thr Val
225                 230                 235                 240

```
Pro Ala Pro Cys Cys Val Pro Ala Ser Tyr Asn Pro Met Val Leu Ile
            245                 250                 255

Gln Lys Thr Asp Thr Gly Val Ser Leu Gln Thr Tyr Asp Asp Leu Leu
        260                 265                 270

Ala Lys Asp Cys His Cys Ile
        275

<210> SEQ ID NO 3
<211> LENGTH: 112
<212> TYPE: PRT
<213> ORGANISM: Homo sapiens

<400> SEQUENCE: 3

Ala Arg Asn Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Met His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 4
<211> LENGTH: 110
<212> TYPE: PRT
<213> ORGANISM: Homo sapiens

<400> SEQUENCE: 4

Asn Gly Asp His Cys Pro Leu Gly Pro Gly Arg Cys Cys Arg Leu His
1               5                   10                  15

Thr Val Arg Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Asn Met His Ala Gln Ile Lys Thr Ser Leu His
    50                  55                  60

Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Asp Leu Leu Ala Lys Asp Cys His Cys Ile
            100                 105                 110

<210> SEQ ID NO 5
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5
```

```
Gln Gly Asp His Cys Pro Leu Gly Pro Gly Arg Cys Cys Arg Leu His
1               5                   10                  15

Thr Val Arg Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Asn Met His Ala Gln Ile Lys Thr Ser Leu His
    50                  55                  60

Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Asp Leu Leu Ala Lys Asp Cys His Cys Ile
            100                 105                 110
```

<210> SEQ ID NO 6
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Asn Gly Asp Asp Cys Pro Leu Gly Pro Gly Arg Cys Cys Arg Leu His
1               5                   10                  15

Thr Val Arg Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Asn Met His Ala Gln Ile Lys Thr Ser Leu His
    50                  55                  60

Arg Leu Lys Pro Asp Thr Val Pro Ala Pro Cys Cys Val Pro Ala Ser
65                  70                  75                  80

Tyr Asn Pro Met Val Leu Ile Gln Lys Thr Asp Thr Gly Val Ser Leu
                85                  90                  95

Gln Thr Tyr Asp Asp Leu Leu Ala Lys Asp Cys His Cys Ile
            100                 105                 110
```

<210> SEQ ID NO 7
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Gln Gly Asp Asp Cys Pro Leu Gly Pro Gly Arg Cys Cys Arg Leu His
1               5                   10                  15

Thr Val Arg Ala Ser Leu Glu Asp Leu Gly Trp Ala Asp Trp Val Leu
            20                  25                  30

Ser Pro Arg Glu Val Gln Val Thr Met Cys Ile Gly Ala Cys Pro Ser
        35                  40                  45

Gln Phe Arg Ala Ala Asn Met His Ala Gln Ile Lys Thr Ser Leu His
    50                  55                  60

Arg Leu Lys Pro Asp Thr Val Pro Ala Pro Cys Cys Val Pro Ala Ser
65                  70                  75                  80
```

Tyr Asn Pro Met Val Leu Ile Gln Lys Thr Asp Thr Gly Val Ser Leu
                85                  90                  95

Gln Thr Tyr Asp Asp Leu Leu Ala Lys Asp Cys His Cys Ile
            100                 105                 110

<210> SEQ ID NO 8
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp His Cys Pro Leu Gly Pro Gly Arg Cys Cys Arg Leu His Thr Val
1               5                   10                  15

Arg Ala Ser Leu Glu Asp Leu Gly Trp Ala Asp Trp Val Leu Ser Pro
            20                  25                  30

Arg Glu Val Gln Val Thr Met Cys Ile Gly Ala Cys Pro Ser Gln Phe
        35                  40                  45

Arg Ala Ala Asn Met His Ala Gln Ile Lys Thr Ser Leu His Arg Leu
    50                  55                  60

Lys Pro Asp Thr Val Pro Ala Pro Cys Cys Val Pro Ala Ser Tyr Asn
65                  70                  75                  80

Pro Met Val Leu Ile Gln Lys Thr Asp Thr Gly Val Ser Leu Gln Thr
                85                  90                  95

Tyr Asp Asp Leu Leu Ala Lys Asp Cys His Cys Ile
            100                 105

<210> SEQ ID NO 9
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Asp Cys Pro Leu Gly Pro Gly Arg Cys Cys Arg Leu His Thr Val
1               5                   10                  15

Arg Ala Ser Leu Glu Asp Leu Gly Trp Ala Asp Trp Val Leu Ser Pro
            20                  25                  30

Arg Glu Val Gln Val Thr Met Cys Ile Gly Ala Cys Pro Ser Gln Phe
        35                  40                  45

Arg Ala Ala Asn Met His Ala Gln Ile Lys Thr Ser Leu His Arg Leu
    50                  55                  60

Lys Pro Asp Thr Val Pro Ala Pro Cys Cys Val Pro Ala Ser Tyr Asn
65                  70                  75                  80

Pro Met Val Leu Ile Gln Lys Thr Asp Thr Gly Val Ser Leu Gln Thr
                85                  90                  95

Tyr Asp Asp Leu Leu Ala Lys Asp Cys His Cys Ile
            100                 105

<210> SEQ ID NO 10
<211> LENGTH: 303
<212> TYPE: PRT
<213> ORGANISM: Mus musculus

<400> SEQUENCE: 10

Met Ala Pro Pro Ala Leu Gln Ala Gln Pro Pro Gly Gly Ser Gln Leu

```
        1               5                  10                 15
Arg Phe Leu Leu Phe Leu Leu Leu Leu Leu Leu Leu Ser Trp Pro
            20                  25                  30

Ser Gln Gly Asp Ala Leu Ala Met Pro Glu Gln Arg Pro Ser Gly Pro
            35                  40                  45

Glu Ser Gln Leu Asn Ala Asp Glu Leu Arg Gly Arg Phe Gln Asp Leu
            50                  55                  60

Leu Ser Arg Leu His Ala Asn Gln Ser Arg Glu Asp Ser Asn Ser Glu
65                  70                  75                  80

Pro Ser Pro Asp Pro Ala Val Arg Ile Leu Ser Pro Glu Val Arg Leu
                85                  90                  95

Gly Ser His Gly Gln Leu Leu Arg Val Asn Arg Ala Ser Leu Ser
            100                 105                 110

Gln Gly Leu Pro Glu Ala Tyr Arg Val His Arg Ala Leu Leu Leu Leu
            115                 120                 125

Thr Pro Thr Ala Arg Pro Trp Asp Ile Thr Arg Pro Leu Lys Arg Ala
            130                 135                 140

Leu Ser Leu Arg Gly Pro Arg Ala Pro Ala Leu Arg Leu Arg Leu Thr
145                 150                 155                 160

Pro Pro Pro Asp Leu Ala Met Leu Pro Ser Gly Gly Thr Gln Leu Glu
                165                 170                 175

Leu Arg Leu Arg Val Ala Ala Gly Arg Gly Arg Arg Ser Ala His Ala
            180                 185                 190

His Pro Arg Asp Ser Cys Pro Leu Gly Pro Gly Arg Cys Cys His Leu
            195                 200                 205

Glu Thr Val Gln Ala Thr Leu Glu Asp Leu Gly Trp Ser Asp Trp Val
            210                 215                 220

Leu Ser Pro Arg Gln Leu Gln Leu Ser Met Cys Val Gly Glu Cys Pro
225                 230                 235                 240

His Leu Tyr Arg Ser Ala Asn Thr His Ala Gln Ile Lys Ala Arg Leu
                245                 250                 255

His Gly Leu Gln Pro Asp Lys Val Pro Ala Pro Cys Cys Val Pro Ser
            260                 265                 270

Ser Tyr Thr Pro Val Val Leu Met His Arg Thr Asp Ser Gly Val Ser
            275                 280                 285

Leu Gln Thr Tyr Asp Asp Leu Val Ala Arg Gly Cys His Cys Ala
            290                 295                 300

<210> SEQ ID NO 11
<211> LENGTH: 112
<212> TYPE: PRT
<213> ORGANISM: Mus musculus

<400> SEQUENCE: 11

Ala His Pro Arg Asp Ser Cys Pro Leu Gly Pro Gly Arg Cys Cys His
1               5                   10                  15

Leu Glu Thr Val Gln Ala Thr Leu Glu Asp Leu Gly Trp Ser Asp Trp
            20                  25                  30

Val Leu Ser Pro Arg Gln Leu Gln Leu Ser Met Cys Val Gly Glu Cys
            35                  40                  45

Pro His Leu Tyr Arg Ser Ala Asn Thr His Ala Gln Ile Lys Ala Arg
            50                  55                  60

Leu His Gly Leu Gln Pro Asp Lys Val Pro Ala Pro Cys Cys Val Pro
65                  70                  75                  80
```

Ser Ser Tyr Thr Pro Val Val Leu Met His Arg Thr Asp Ser Gly Val
                85                  90                  95

Ser Leu Gln Thr Tyr Asp Asp Leu Val Ala Arg Gly Cys His Cys Ala
            100                 105                 110

<210> SEQ ID NO 12
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ser Cys Pro Leu Gly Pro Gly Arg Cys Cys His Leu Glu Thr Val
1               5                   10                  15

Gln Ala Thr Leu Glu Asp Leu Gly Trp Ser Asp Trp Val Leu Ser Pro
            20                  25                  30

Arg Gln Leu Gln Leu Ser Met Cys Val Gly Glu Cys Pro His Leu Tyr
        35                  40                  45

Arg Ser Ala Asn Thr His Ala Gln Ile Lys Ala Arg Leu His Gly Leu
    50                  55                  60

Gln Pro Asp Lys Val Pro Ala Pro Cys Cys Val Pro Ser Ser Tyr Thr
65                  70                  75                  80

Pro Val Val Leu Met His Arg Thr Asp Ser Gly Val Ser Leu Gln Thr
                85                  90                  95

Tyr Asp Asp Leu Val Ala Arg Gly Cys His Cys Ala
            100                 105

<210> SEQ ID NO 13
<211> LENGTH: 924
<212> TYPE: DNA
<213> ORGANISM: Homo sapiens

<400> SEQUENCE: 13
atgcccgggc aagaactcag gacggtgaat ggctctcaga tgctcctggt gttgctggtg      60
ctctcgtggc tgccgcatgg gggcgccctg tctctggccg aggcgagccg cgcaagtttc     120
ccgggaccct cagagttgca ctccgaagac tccagattcc gagagttgcg gaaacgctac     180
gaggacctgc taaccaggct gcgggccaac cagagctggg aagattcgaa caccgacctc     240
gtcccggccc ctgcagtccg atactcacg ccagaagtgc ggctgggatc cggcggccac     300
ctgcacctgc gtatctctcg ggccgccctt cccgagggc tccccgaggc ctcccgcctt     360
caccgggctc tgttccggct gtccccgacg gcgtcaaggt cgtgggacgt gacacgaccg     420
ctgcggcgtc agctcagcct tgcaagaccc caggcacccg cgctgcacct gcgactgtcg     480
ccgccgccgt cgcagtcgga ccaactgctg gcagaatctt cgtccgcacg gccccagctg     540
gagttgcact gcggccgcca agccgccagg gggcgccgca gagcgcgtgc gcgcaacggg     600
gaccactgtc cgctcgggcc cgggcgttgc tgccgtctgc acacggtccg cgcgtcgctg     660
gaagacctgg gctgggccga ttgggtgctg tcgccacggg aggtgcaagt gaccatgtgc     720
atcggcgcgt gcccgagcca gttccggggcg gcaaacatgc acgcgcagat caagacgagc     780
ctgcaccgcc tgaagcccga cacggtgcca gcgccctgct gcgtgccgc cagctacaat     840 cccatggtgc tcattcaaaa gaccgacacc ggggtgtcac tccagaccta tgatgacttg     900
ttagccaaag actgccactg cata                                             924

```
<210> SEQ ID NO 14
<211> LENGTH: 909
<212> TYPE: DNA
<213> ORGANISM: Mus musculus

<400> SEQUENCE: 14
atggccccgc cgcgctcca ggcccagcct ccaggcggct ctcaactgag gttcctgctg      60
ttcctgctgc tgttgctgct gctgctgtca tggccatcgc aggggacgc cctggcaatg     120 cctgaacagc gaccctccgg ccctgagtcc caactcaacg ccgacgagct acggggtcgc    180
ttccaggacc tgctgagccg gctgcatgcc aaccagagcc gagaggactc gaactcagaa    240
ccaagtcctg acccagctgt ccggatactc agtccagagg tgagattggg gtcccacggc    300
cagctgctac tccgcgtcaa ccgggcgtcg ctgagtcagg gtctccccga agcctaccgc    360
gtgcaccgag cgctgctcct gctgacgccg acggcccgcc cctgggacat cactaggccc    420
ctgaagcgtg cgctcagcct ccggggaccc cgtgctcccg cattacgcct gcgcctgacg    480
ccgcctccgg acctggctat gctgccctct ggcggcacgc agctggaact gcgcttacgg    540
gtagccgccg gcagggggcg ccgaagcgcg catgcgcacc aagagactc gtgcccactg     600 ggtccagggc gctgctgtca cttggagact gtgcaggcaa ctcttgaaga cttgggctgg    660
agcgactggg tgctgtcccc gcgccagctg cagctgagca tgtgcgtggg cgagtgtccc    720
cacctgtatc gctccgcgaa cacgcatgcg cagatcaaag cacgcctgca tggcctgcag    780
cctgacaagg tgcctgcccc gtgctgtgtc ccctccagct acacccggt ggttcttatg     840 cacaggacag acagtggtgt gtcactgcag acttatgatg acctggtggc ccggggctgc    900
cactgcgct                                                            909

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 15

His His His His His His
1               5
```

METHODS AND COMPOSITIONS USING GDF15 POLYPEPTIDES FOR INCREASING RED BLOOD CELLS

CROSS-REFERENCE TO RELATED APPLICATIONS

This application is a United States National Stage Application under 35 U.S.C. § 371 of International Application No. PCT/US2015/058116 (pending), filed Oct. 29, 2015, which claims the benefit of priority to U.S. Provisional Application No. 62/072,889, filed Oct. 30, 2014. The specification of these applications are hereby incorporated by reference in their entirety.

SEQUENCE LISTING

The instant application contains a Sequence Listing which has been submitted electronically in ASCII format and is hereby incorporated by reference in its entirety. Said ASCII copy, created on Aug. 22, 2017, is named 1848179-0002-082-301_SL.txt and is 20,472 bytes in size.

BACKGROUND OF THE INVENTION

The mature red blood cell (RBC), or erythrocyte, is responsible for oxygen transport in the circulatory systems of vertebrates. Red blood cells contain high concentrations of hemoglobin, a protein that binds oxygen in the lungs at relatively high partial pressure of oxygen ($pO_2$) and delivers oxygen to areas of the body with a relatively low $pO_2$.

Mature red blood cells are produced from pluripotent hematopoietic stem cells in a process termed erythropoiesis. Postnatal erythropoiesis occurs primarily in the bone marrow and in the red pulp of the spleen. The coordinated action of various signaling pathways control the balance of cell proliferation, differentiation, survival and death. Under normal conditions, red blood cells are produced at a rate that maintains a constant red cell mass in the body, and production may increase or decrease in response to various stimuli, including increased or decreased oxygen tension or tissue demand. The process of erythropoiesis begins with the formation of lineage committed precursor cells and proceeds through a series of distinct precursor cell types. The final stages of erythropoiesis occur as reticulocytes are released into the bloodstream and lose their mitochondria and ribosomes while assuming the morphology of mature red blood cell. An elevated level of reticulocytes, or an elevated reticulocyte:erythrocyte ratio, in the blood is indicative of increased red blood cell production rates.

Erythropoietin (EPO) is widely recognized as the most significant positive regulator of postnatal erythropoiesis in vertebrates. EPO regulates the compensatory erythropoietic response to reduced tissue oxygen tension (hypoxia) and low red blood cell levels or low hemoglobin levels. In humans, elevated EPO levels promote red blood cell formation by stimulating the generation of erythroid progenitors in the bone marrow and spleen. In the mouse, EPO enhances erythropoiesis primarily in the spleen.

Anemia is a broadly-defined condition characterized by lower than normal levels of hemoglobin or red blood cells in the blood. In some instances, anemia is caused by a primary disorder in the production or survival of red blood cells. More commonly, anemia is secondary to diseases of other systems (Weatherall & Provan (2000) Lancet 355, 1169-1175). Anemia may result from a reduced rate of production or increased rate of destruction of red blood cells or by loss of red blood cells due to bleeding. Anemia may result from a variety of disorders that include, for example, chronic renal failure, chemotherapy treatment, myelodysplastic syndrome, rheumatoid arthritis, and bone marrow transplantation.

Treatment with EPO typically causes a rise in hemoglobins by about 1-3 g/dL in healthy humans over a period of weeks. When administered to anemic individuals, this treatment regimen often provides substantial increases in hemoglobin and red blood cell levels and leads to improvements in quality of life and prolonged survival. EPO is not uniformly effective, and many individuals are refractory to even high doses (Horl et al. (2000) Nephrol Dial Transplant 15, 43-50). Over 50% of patients with cancer have an inadequate response to EPO, approximately 10% with end-stage renal disease are hyporesponsive (Glaspy et al. (1997) J Clin Oncol 15, 1218-1234; Demetri et al. (1998) J Clin Oncol 16, 3412-3425), and less than 10% with myelodysplastic syndrome respond favorably (Estey (2003) Curr Opin Hematol 10, 60-67). Several factors, including inflammation, iron and vitamin deficiency, inadequate dialysis, aluminum toxicity, and hyperparathyroidism may predict a poor therapeutic response. The molecular mechanisms of resistance to EPO are as yet unclear. Recent evidence suggests that higher doses of EPO may be associated with an increased risk of cardiovascular morbidity, tumor growth, and mortality in some patient populations (Krapf et al., 2009, Clin J Am Soc Nephrol 4:470-480; Glaspy, 2009, Annu Rev Med 60:181-192). It has therefore been recommended that EPO-based therapeutic compounds (erythropoietin-stimulating agents, ESAs) be administered at the lowest dose sufficient to avoid the need for red blood cell transfusions (Jelkmann et al., 2008, Crit Rev Oncol. Hematol 67:39-61).

Thus, it is an object of the present disclosure to provide alternative methods and compositions for increasing red blood cell levels in patients.

SUMMARY OF THE INVENTION

In part, the disclosure demonstrates that GDF15 polypeptides may be used to increase red blood cell and hemoglobin levels. In particular, the disclosure demonstrates that GDF15, when administered in vivo, causes a robust and rapid increase in red blood cell levels, hematocrit and hemoglobin. Therefore, in certain embodiments, the disclosure provides methods for using GDF15 polypeptides to increase red blood cell and hemoglobin levels in patients and to treat disorders associated with low red blood cell or hemoglobin levels in patients in need thereof. In some embodiments, the disclosure provides methods for using GDF15 polypeptides, alone or in combination with one or more EPO receptor activators, to treat or prevent anemia in a patient in need thereof. For example, GDF15 polypeptides, alone or in combination with one or more EPO receptor activators, may be used to treat or prevent anemia in patients wherein the anemia is associated with one or more of cancer, kidney (renal) disease (e.g., chronic kidney disease or end-stage kidney disease or failure), chemotherapy treatment (e.g., treatment with a taxane), inflammation, or as consequence of blood loss. In some embodiments, GDF15 polypeptides, alone or in combination with one or more EPO receptor activators, may be used to treat ineffective erythropoiesis. For example, in some embodiments, a GDF15 polypeptide, alone or in combination with one or more EPO receptor activators, may be used to treat a thalassemia syndrome (e.g., β-thalassemia), including treating or preventing one or more complications (manifestations) of a thalassemia syndrome. In other embodiments, a GDF15 polypeptide, alone or in combination with one or more EPO receptor activators, may be used to treat sickle-cell disease, including treating or preventing one or more complications of a sickle-cell disease. In some embodiments, a GDF15 polypeptide, alone or in combination with one or more EPO receptor activators, may be used to treat myelodysplastic syndrome, including treating or preventing one or more complications of myelodysplastic syndrome.

In part, the disclosure demonstrates that GDF15 polypeptides may be used in combination (e.g., administered at the same time or different times, but generally in such a manner as to achieve overlapping pharmacological effects) with EPO receptor activators to increase red blood cell levels (erythropoiesis) or treat anemia in patients in need thereof. In part, the disclosure demonstrates that a GDF15 polypeptide can be administered in combination with an EPO receptor activator to synergistically increase formation of red blood cells in a patient. Thus, the effect of this combined treatment can be significantly greater than the sum of the effects of the GDF15 polypeptide and the EPO receptor activator when administered separately at their respective doses. In certain embodiments, this synergism may be advantageous since it enables target levels of red blood cells to be attained with lower doses of an EPO receptor activator, thereby avoiding potential adverse effects or other problems associated with higher levels of EPO receptor activation.

An EPO receptor activator may stimulate erythropoiesis by directly contacting and activating EPO receptor. In certain embodiments, the EPO receptor activator is one of a class of compounds based on the 165 amino-acid sequence of native EPO and generally known as erythropoiesis-stimulating agents (ESAs), examples of which are epoetin alfa, epoetin beta, epoetin delta, and epoetin omega. In other embodiments, ESAs include synthetic EPO proteins (SEPs) and EPO derivatives with nonpeptidic modifications conferring desirable pharmacokinetic properties (lengthened circulating half-life), examples of which are darbepoetin alfa and methoxy-polyethylene-glycol epoetin beta. In certain embodiments, an EPO receptor activator may be an EPO receptor agonist that does not incorporate the EPO polypeptide backbone or is not generally classified as an ESA. Such EPO receptor agonists may include, but are not limited to, peptidic and nonpeptidic mimetics of EPO, agonistic antibodies targeting EPO receptor, fusion proteins comprising an EPO mimetic domain, and erythropoietin receptor extended-duration limited agonists (EREDLA).

In certain embodiments, an EPO receptor activator may stimulate erythropoiesis indirectly, without contacting EPO receptor itself, by enhancing production of endogenous EPO. For example, hypoxia-inducible transcription factors (HIFs) are endogenous stimulators of EPO gene expression that are suppressed (destabilized) under normoxic conditions by cellular regulatory mechanisms. In part, the disclosure provides increased erythropoiesis in a patient by combined treatment with a GDF15 and an indirect EPO receptor activator with HIF stabilizing properties, such as a prolyl hydroxylase inhibitor.

In certain aspects, the present disclosure provides GDF15 polypeptides. In some embodiments, a GDF15 polypeptide has an amino acid sequence that comprises, consists of, or consists essentially of, the amino acid sequence of SEQ ID NO: 1, or an amino acid sequence that is at least 68%, 70%, 75%, 80%, 85%, 90%, 91%, 92%, 93%, 94%, 95%, 96%, 97%, 98%, or 99% identical to the amino acid sequence of SEQ ID NO: 1. In some embodiments, a GDF15 polypeptide has an amino acid sequence that comprises, consists of, or consists essentially of, the amino acid sequence of SEQ ID NO: 2, or an amino acid sequence that is at least 68%, 70%, 75%, 80%, 85%, 90%, 91%, 92%, 93%, 94%, 95%, 96%, 97%, 98%, or 99% identical to the amino acid sequence of SEQ ID NO: 2. In some embodiments, a GDF15 polypeptide has an amino acid sequence that comprises, consists of, or consists essentially of, the amino acid sequence of SEQ ID NO: 3, or an amino acid sequence that is at least 68%, 70%, 75%, 80%, 85%, 90%, 91%, 92%, 93%, 94%, 95%, 96%, 97%, 98%, or 99% identical to the amino acid sequence of SEQ ID NO: 3. In some embodiments, a GDF15 polypeptide has an amino acid sequence that comprises, consists of, or consists essentially of, the amino acid sequence of SEQ ID NO: 4, or an amino acid sequence that is at least 68%, 70%, 75%, 80%, 85%, 90%, 91%, 92%, 93%, 94%, 95%, 96%, 97%, 98%, or 99% identical to the amino acid sequence of SEQ ID NO: 4. In some embodiments, a GDF15 polypeptide has an amino acid sequence that comprises, consists of, or consists essentially of, the amino acid sequence of SEQ ID NO: 5, or an amino acid sequence that is at least 68%, 70%, 75%, 80%, 85%, 90%, 91%, 92%, 93%, 94%, 95%, 96%, 97%, 98%, or 99% identical to the amino acid sequence of SEQ ID NO: 5. In some embodiments, a GDF15 polypeptide has an amino acid sequence that comprises, consists of, or consists essentially of, the amino acid sequence of SEQ ID NO: 6, or an amino acid sequence that is at least 68%, 70%, 75%, 80%, 85%, 90%, 91%, 92%, 93%, 94%, 95%, 96%, 97%, 98%, or 99% identical to the amino acid sequence of SEQ ID NO: 6. In some embodiments, a GDF15 polypeptide has an amino acid sequence that comprises, consists of, or consists essentially of, the amino acid sequence of SEQ ID NO: 7, or an amino acid sequence that is at least 68%, 70%, 75%, 80%, 85%, 90%, 91%, 92%, 93%, 94%, 95%, 96%, 97%, 98%, or 99% identical to the amino acid sequence of SEQ ID NO: 7. In some embodiments, a GDF15 polypeptide has an amino acid sequence that comprises, consists of, or consists essentially of, the amino acid sequence of SEQ ID NO: 8, or an amino acid sequence that is at least 68%, 70%, 75%, 80%, 85%, 90%, 91%, 92%, 93%, 94%, 95%, 96%, 97%, 98%, or 99% identical to the amino acid sequence of SEQ ID NO: 8. In some embodiments, a GDF15 polypeptide has an amino acid sequence that comprises, consists of, or consists essentially of, the amino acid sequence of SEQ ID NO: 9, or an amino acid sequence that is at least 68%, 70%, 75%, 80%, 85%, 90%, 91%, 92%, 93%, 94%, 95%, 96%, 97%, 98%, or 99% identical to the amino acid sequence of SEQ ID NO: 9. In some embodiments, a GDF15 polypeptide has an amino acid sequence that comprises, consists of, or consists essentially of, the amino acid sequence of SEQ ID NO: 10, or an amino acid sequence that is at least 68%, 70%, 75%, 80%, 85%, 90%, 91%, 92%, 93%, 94%, 95%, 96%, 97%, 98%, or 99% identical to the amino acid sequence of SEQ ID NO: 10. In some embodiments, a GDF15 polypeptide has an amino acid sequence that comprises, consists of, or consists essentially of, the amino acid sequence of SEQ ID NO: 11, or an amino acid sequence that is at least 68%, 70%, 75%, 80%, 85%, 90%, 91%, 92%, 93%, 94%, 95%, 96%, 97%, 98%, or 99% identical to the amino acid sequence of SEQ ID NO: 11. In some embodiments, a GDF15 polypeptide has an amino acid sequence that comprises, consists of, or consists essentially of, the amino acid sequence of SEQ ID NO: 12, or an amino acid sequence that is at least 68%, 70%, 75%, 80%, 85%, 90%, 91%, 92%, 93%, 94%, 95%, 96%, 97%, 98%, or 99% identical to the amino acid sequence of SEQ ID NO: 12. A GDF15 polypeptide may comprise an amino acid sequence that is encoded by a nucleic acid of SEQ ID NO: 13, including any portion thereof, such as nucleotides 589-924 that encode the mature portion of GDF15, and a GDF15 polypeptide may be encoded by a nucleic acid that hybridizes to a nucleic acid that is complementary to the sequence of nucleotides 589-924 of SEQ ID NO: 13 under less stringent, moderately stringent or highly stringent hybridization conditions.

In certain aspects, the disclosure provides pharmaceutical preparations comprising a GDF15 polypeptide and a pharmaceutically acceptable carrier. The GDF15 polypeptide may bind to one or more type I (e.g., ALK5) or type II receptors with a $K_D$ less than 10 micromolar, less than 1 micromolar, less than 100 nanomolar, less than 10 nanomolar, or less than 1 nanomolar. Typically, a GDF15 polypeptide will bind to both a type I receptor and a type II receptor, although binding to one of the receptors may be at a very weak affinity. Optionally, the GDF15 polypeptide will stimulate expression from a SMAD2- or SMAD3-responsive promoter in a cell, such as a promoter containing the CAGA-12 responsive element derived from the PAI-1 gene.

A pharmaceutical preparation may further comprise a GDF15 prodomain polypeptide. In certain embodiments, a GDF15 prodomain polypeptide has an amino acid sequence that comprises, consists of, or consists essentially of, the amino acid sequence of 1-196 of SEQ ID NO: 1 or an amino acid sequence that is at least 68%, 70%, 75%, 80%, 85%, 90%, 91%, 92%, 93%, 94%, 95%, 96%, 97%, 98%, or 99% identical to same. A GDF15 prodomain polypeptide may comprise an amino acid sequence that is encoded by the sequence of nucleotides 88-588 of SEQ ID NO: 13, including any portion thereof, and a GDF15 prodomain polypeptide may be encoded by a nucleic acid that hybridizes to a nucleic acid that is complementary to the sequence of nucleotides 88-588 of SEQ ID NO: 13 under less stringent, moderately stringent or highly stringent hybridization conditions. A prodomain polypeptide may be covalently or non-covalently associated with a GDF15 polypeptide.

Preferably, a pharmaceutical preparation is substantially pyrogen-free. In general, it is preferable that a GDF15 polypeptide be expressed in a mammalian cell line that mediates suitably natural glycosylation so as to diminish the likelihood of an unfavorable immune response in a patient. Human and CHO cell lines have been used successfully, and it is expected that other common mammalian expression vectors will be useful.

In certain aspects, the disclosure provides methods for making a GDF15 polypeptide. Such a method may include expressing any of the nucleic acids (e.g., SEQ ID NO: 13 or 14) disclosed herein in a suitable cell, such as a Chinese hamster ovary (CHO) cell. Such a method may comprise: a) culturing a cell under conditions suitable for expression of the GDF15 polypeptide, wherein said cell is transformed with a GDF15 expression construct; and b) recovering the GDF15 polypeptide so expressed. GDF15 polypeptides may be recovered as crude, partially purified, or highly purified fractions using any of the well-known techniques for obtaining protein from cell cultures. Purification may be achieved by one or more chromatographic steps comprising cation exchange, anion exchange, and reverse-phase HPLC. Purification may also be achieved by contacting the GDF15 polypeptide with a ligand binding domain of a receptor protein or modified version thereof that binds to GDF15. The ligand binding domain may, for example, be used as a fusion with an Fc portion of an IgG (optionally with an intervening linker) and immobilized on a protein A-coated surface.

In certain aspects, a GDF15 polypeptide, or a pharmaceutical preparation comprising one or more of the foregoing, may be used in a method for promoting red blood cell production or increasing red blood cell levels in a subject. In certain embodiments, the disclosure provides methods for treating a disorder associated with low red blood cell counts or low hemoglobin levels (e.g., an anemia), or to promote red blood cell production, in patients in need thereof. A method may comprise administering to a subject in need thereof an effective amount of a GDF15 polypeptide. In certain aspects, the disclosure provides uses of GDF15 polypeptides for making a medicament for the treatment of a disorder or condition as described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 depicts aligned amino acid sequences of mature GDF15 protein from mouse (mGDF15, SEQ ID NO: 11) and human (hGDF15, SEQ ID NO: 3). Asterisks denote fully conserved residues.

DETAILED DESCRIPTION OF THE INVENTION

1. Overview

Figure 2:
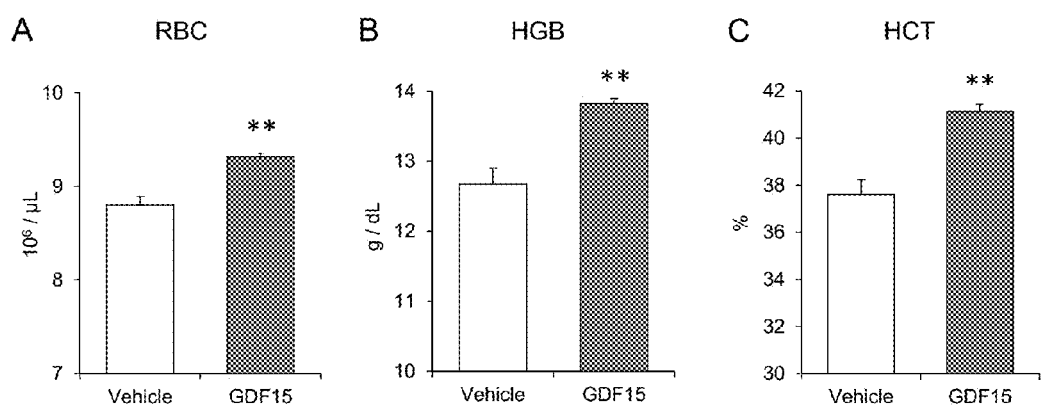
FIG. 2 depicts the effect of recombinant murine GDF15 (0.3 mg/kg) or vehicle (Tris-buffered saline, TBS) administered every other day for 3 weeks on red blood cell number (A), hemoglobin concentration (B), and hematocrit (C) in wild-type mice. Data are means±SEM; n=3-5 mice per group; **, P<0.01.

EPO is a glycoprotein hormone involved in the growth and maturation of erythroid progenitor cells into erythrocytes. EPO is produced by the liver during fetal life and by the kidney in adults. Decreased production of EPO, which commonly occurs in adults as a consequence of renal failure, leads to anemia. EPO has been produced by genetic engineering techniques based on expression and secretion of the protein from a host cell transfected with the EPO gene. Administration of such recombinant EPO has been effective in the treatment of anemia. For example, Eschbach et al. (1987, N Engl J Med 316:73) describe the use of EPO to correct anemia caused by chronic renal failure.

Effects of EPO are mediated through its binding to, and activation of, a cell surface receptor belonging to the cytokine receptor superfamily and designated the EPO receptor. The human and murine EPO receptors have been cloned and expressed (D'Andrea et al., 1989, Cell 57:277; Jones et al., 1990, Blood 76:31; Winkelman et al., 1990, Blood 76:24; WO 90/08822/U.S. Pat. No. 5,278,065). The human EPO receptor gene encodes a 483 amino acid transmembrane protein comprising an extracellular domain of approximately 224 amino acids and exhibits approximately 82% amino acid sequence identity with the murine EPO receptor (See U.S. Pat. No. 6,319,499). The cloned, full-length EPO receptor expressed in mammalian cells (66-72 kDa) binds EPO with an affinity ($K_D$=100-300 nM) similar to that of the native receptor on erythroid progenitor cells. Thus, this form is thought to contain the main EPO binding determinant and is referred to as the EPO receptor. By analogy with other closely related cytokine receptors, the EPO receptor is thought to dimerize upon agonist binding. Nevertheless, the detailed structure of the EPO receptor, which may be a multimeric complex, and its specific mechanism of activation are not completely understood (U.S. Pat. No. 6,319,499).

Activation of the EPO receptor results in several biological effects. These include increased proliferation of immature erythroblasts, increased differentiation of immature erythroblasts, and decreased apoptosis in erythroid progenitor cells (Liboi et al., 1993, Proc Natl Acad Sci USA 90:11351-11355; Koury et al., 1990, Science 248:378-381). The EPO receptor signal transduction pathways mediating proliferation and differentiation appear to be distinct (Noguchi et al., 1988, Mol Cell Biol 8:2604; Patel et al., 1992, J Biol Chem 1992, 267:21300; Liboi et al., ibid). Some results suggest that an accessory protein may be required for mediation of the differentiation signal (Chiba et al., 1993, Nature 362:646; Chiba et al., 1993, Proc Natl Acad Sci USA 90:11593); however, there is controversy regarding the role of accessory proteins in differentiation since a constituitively activated form of the receptor can stimulate both proliferation and differentiation (Pharr et al., 1993, Proc Natl Acad Sci USA 90:938).

EPO receptor activators include small-molecule erythropoiesis-stimulating agents (ESAs) as well as EPO-based compounds. An example of the former is a dimeric peptide-based agonist covalently linked to polyethylene glycol (proprietary name Hematide), which has shown erythropoiesis-stimulating properties in healthy volunteers and in patients with both chronic kidney disease and endogenous anti-EPO antibodies (Stead et al., 2006, Blood 108:1830-1834; Macdougall et al., 2009, N Engl J Med 361:1848-1855). Other examples include nonpeptide-based ESAs (Qureshi et al., 1999, Proc Natl Acad Sci USA 96:12156-12161).

EPO receptor activators also include compounds that stimulate erythropoiesis indirectly, without contacting EPO receptor itself, by enhancing production of endogenous EPO. For example, hypoxia-inducible transcription factors (HIFs) are endogenous stimulators of EPO gene expression that are suppressed (destabilized) under normoxic conditions by cellular regulatory mechanisms. Therefore, inhibitors of HIF prolyl hydroxylase enzymes are being investigated for EPO-inducing activity in vivo. Other indirect activators of EPO receptor include inhibitors of GATA-2 transcription factor (Nakano et al., 2004, Blood 104:4300-4307), which tonically inhibits EPO gene expression, and inhibitors of hemopoietic cell phosphatase (HCP or SHP-1), which functions as a negative regulator of EPO receptor signal transduction (Klingmuller et al., 1995, Cell 80:729-738).

The transforming growth factor-β (TGFβ) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. By manipulating the activity of a member of the TGFβ family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat Genet. 1997, 17(1):71-4. Furthermore, in humans, inactive alleles of GDF8 are associated with increased muscle mass and, reportedly, exceptional strength. Schuelke et al., N Engl J Med 2004, 350:2682-8.

GDF15 is a member of the TGFβ superfamily that is produced as a disulfide-linked homodimer and can act near its site of production (locally) or at a distance via circulation in the blood. GDF15 signals are mediated by heteromeric complexes of type I and type II serine/threonine kinase receptors, which phosphorylate and activate downstream Smad proteins upon ligand stimulation (Massagué, 2000, Nat. Rev. Mol. Cell Biol. 1:169-178). These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling, and type II receptors are required for binding ligands and for expression of type I receptors. In some cases, type III receptors (also known as co-receptors/accessory proteins) facilitate ligand binding to type II receptor or otherwise modify ligand signaling. Upon ligand binding, type I and II receptors form a stable complex resulting in phosphorylation of type I receptor by type II receptor.

As demonstrated herein, a GDF15 polypeptide is effective at promoting red blood cell formation ex vivo, increasing red blood cell levels in vivo, and acting synergistically with EPO to increase red blood cell levels in vivo. Therefore, GDF15 polypeptides are expected to have beneficial effects in a variety of models for anemia. It should be noted that hematopoiesis is a complex process, regulated by a variety of factors, including EPO, G-CSF and iron homeostasis. The terms "increase red blood cell levels" and "promote red blood cell formation" refer to clinically observable metrics, such as hematocrit, red blood cell numbers (counts) and hemoglobin concentration measurements, and are intended to be neutral as to the mechanism by which such changes occur.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "Δ") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

2. GDF15 Polypeptides and Nucleic Acids

In certain aspects, the invention relates to GDF15 polypeptides, including, for example, mature human GDF15 protein as well as GDF15 polypeptides that retain the prodomain, whether covalently or non-covalently attached, and variants and truncations of the foregoing. Such variations and truncations may be selected to retain the ability to stimulate signaling by one or more of the known receptors for GDF15, including and ALK5. Optionally, a GDF15 polypeptide can increase expression of luciferase in a cell line transfected with a CAGA-12 luciferase reporter gene construct.

As used herein, the term "GDF15" refers to the family of GDF15 proteins, respectively, from any species and variants derived from such proteins by mutagenesis, truncation, or other modification. GDF15 proteins are moderately divergent across vertebrate lineages, including the mature portion of the protein, as shown in FIG. 1.

The term "GDF15 polypeptide" includes polypeptides comprising any naturally occurring polypeptide of a GDF15 family member, respectively, as well as any variants thereof (including mutants, fragments, fusions, and peptidomimetic forms) that retain a useful activity. For example, GDF15 polypeptides may comprise polypeptides derived from the sequence of any known GDF15 protein and may include forms expressed with a signal peptide, as a proprotein form (containing both the prodomain and the mature portion), and as the fully mature form. As shown in FIG. 1, the mature GDF15 proteins in humans and mice are moderately divergent (68% identical at the amino acid level), and therefore functional variants may, for example, be selected by reference to amino acids that are less conserved among different vertebrate species as such changes will generally be tolerated. GDF15 polypeptides may comprise, consist essentially of, or consist of, an amino acid sequence that is at least 68%, 70%, 75%, 80%, 85%, 90%, 95%, 97%, 98%, 99%, or 100% identical to the sequence of a naturally occurring GDF15 polypeptide such as any of SEQ ID NOs. 1, 2, 3, 4, 5, 6, 7, 8, 9, 10, 11, or 12. Numbering of amino acids for all human GDF15 polypeptides described herein is based on the numbering for SEQ ID NO:1, unless specifically designated otherwise.

Examples of GDF15 polypeptides include:

Full-length human GDF15 precursor protein with the native leader included (SEQ ID NO: 1), corresponding to amino acids 1-308 of NCBI Reference Sequence No. NP_004855.2. The leader is denoted by dashed underline, and the mature GDF15 sequence is indicated by solid underline.

```
                                                        (SEQ ID NO: 1)
  1 MPGQELRTVN GSQMLLVLLV LSWLPHGGAL SLAEASRASF PGPSELHSED

51 SRFRELRKRY EDLLTRLRAN QSWEDSNTDL VPAPAVRILT PEVRLGSGGH

101 LHLRISRAAL PEGLPEASRL HRALFRLSPT ASRSWDVTRP LRRQLSLARP

151 QAPALHLRLS PPPSQSDQLL AESSSARPQL ELHLRPQAAR GRRRARARNG

201 DHCPLGPGRC CRLHTVRASL EDLGWADWVL SPREVQVTMC IGACPSQFRA

251 ANMHAQIKTS LHRLKPDTVP APCCVPASYN PMVLIQKTDT GVSLQTYDDL

301 LAKDCHCI
```

Full-length human GDF15 precursor protein with the leader removed (SEQ ID NO: 2), corresponding to amino acids 30-308 of SEQ ID NO: 1. The GDF15 prodomain is unmarked while the mature GDF15 sequence is underlined.

```
                                                  (SEQ ID NO: 2)
  1  LSLAEASRAS FPGPSELHSE DSRFRELRKR YEDLLTRLRA NQSWEDSNTD

51  LVPAPAVRIL TPEVRLGSGG HLHLRISRAA LPEGLPEASR LHRALFRLSP

101  TASRSWDVTR PLRRQLSLAR PQAPALHLRL SPPPSQSDQL LAESSSARPQ

151  LELHLRPQAA RGRRRARARN GDHCPLGPGR CCRLHTVRAS LEDLGWADWV

201  LSPREVQVTM CIGACPSQFR AANMHAQIKT SLHRLKPDTV PAPCCVPASY

251  NPMVLIQKTD TGVSLQTYDD LLAKDCHCI
```

Predicted full-length mature human GDF15 (SEQ ID NO: 3) corresponding to amino acids 197-308 of SEQ ID NO: 1.

```
                                                  (SEQ ID NO: 3)
  1  ARNGDHCPLG PGRCCRLHTV RASLEDLGWA DWVLSPREVQ VTMCIGACPS

51  QFRAANMHAQ IKTSLHRLKP DTVPAPCCVP ASYNPMVLIQ KTDTGVSLQT

101  YDDLLAKDCH CI
```

Purified version of mature human GDF15 (SEQ ID NO: 4) corresponding to amino acids 199-308 of SEQ ID NO: 1.

```
                                                  (SEQ ID NO: 4)
  1  NGDHCPLGPG RCCRLHTVRA SLEDLGWADW VLSPREVQVT MCIGACPSQF

51  RAANMHAQIK TSLHRLKPDT VPAPCCVPAS YNPMVLIQKT DTGVSLQTYD

101  DLLAKDCHCI
```

In certain aspects, GDF15 polypeptides include functional variants or modified forms comprising amino acid substitutions or deletions. Thus, additional examples of GDF15 polypeptides include:

A variant of purified mature human GDF15 corresponding to amino acids 199-308 of SEQ ID NO: 1 with a N199Q substitution (SEQ ID NO: 5, underlined) as disclosed in PCT Patent Publication No. WO 2013/113008.

```
                                                  (SEQ ID NO: 5)
  1  QGDHCPLGPG RCCRLHTVRA SLEDLGWADW VLSPREVQVT MCIGACPSQF

51  RAANMHAQIK TSLHRLKPDT VPAPCCVPAS YNPMVLIQKT DTGVSLQTYD

101  DLLAKDCHCI
```

A second variant of purified mature human GDF15 corresponding to amino acids 199-308 of SEQ ID NO: 1 with a H202D substitution (SEQ ID NO: 6, underlined) as disclosed in PCT Patent Publication No. WO 2013/113008.

```
                                                  (SEQ ID NO: 6)
  1  NGDDCPLGPG RCCRLHTVRA SLEDLGWADW VLSPREVQVT MCIGACPSQF

51  RAANMHAQIK TSLHRLKPDT VPAPCCVPAS YNPMVLIQKT DTGVSLQTYD

101  DLLAKDCHCI
```

A third variant of purified mature human GDF15 corresponding to amino acids 199-308 of SEQ ID NO: 1 with both N199Q and H202D substitutions (SEQ ID NO: 7, underlined).

```
                                            (SEQ ID NO: 7)
  1  QGDDCPLGPG RCCRLHTVRA SLEDLGWADW VLSPREVQVT MCIGACPSQF

51  RAANMHAQIK TSLHRLKPDT VPAPCCVPAS YNPMVLIQKT DTGVSLQTYD

101  DLLAKDCHCI
```

An N'Δ4 variant of mature human GDF15 (SEQ ID NO: 8) corresponding to amino acids 201-308 of SEQ ID NO: 1.

```
                                            (SEQ ID NO: 8)
  1  DHCPLGPGRC CRLHTVRASL EDLGWADWVL SPREVQVTMC IGACPSQFRA

51  ANMHAQIKTS LHRLKPDTVP APCCVPASYN PMVLIQKTDT GVSLQTYDDL

101  LAKDCHCI
```

An N'Δ4 variant of mature human GDF15 corresponding to amino acids 201-308 of SEQ ID NO: 1 with a H202D substitution (SEQ ID NO: 9).

```
                                            (SEQ ID NO: 9)
  1  DDCPLGPGRC CRLHTVRASL EDLGWADWVL SPREVQVTMC IGACPSQFRA

51  ANMHAQIKTS LHRLKPDTVP APCCVPASYN PMVLIQKTDT GVSLQTYDDL

101  LAKDCHCI
```

Full-length mouse GDF15 precursor protein with the native leader included (SEQ ID NO: 10), corresponding to amino acids 1-303 of NCBI Reference Seq. No. NP_035949.2. The leader is denoted by dashed underline, and the mature GDF15 sequence is indicated by solid underline.

```
                                           (SEQ ID NO: 10)
  1  MAPPALQAQP PGGSQLRFLL FLLLLLLLLS WPSQGDALAM PEQRPSGPES

51  QLNADELRGR FQDLLSRLHA NQSREDSNSE PSPDPAVRIL SPEVRLGSHG

101  QLLLRVNRAS LSQGLPEAYR VHRALLLLTP TARPWDITRP LKRALSLRGP

151  RAPALRLRLT PPPDLAMLPS GGTQLELRLR VAAGRGRRSA HAHPRDSCPL

201  GPGRCCHLET VQATLEDLGW SDWVLSPRQL QLSMCVGECP HLYRSANTHA

251  QIKARLHGLQ PDKVPAPCCV PSSYTPVVLM HRTDSGVSLQ TYDDLVARGC

301  HCA
```

Full-length mature mouse GDF15 (SEQ ID NO: 11) corresponding to amino acids 192-303 of SEQ ID NO: 10.

```
                                           (SEQ ID NO: 11)
  1  AHPRDSCPLG PGRCCHLETV QATLEDLGWS DWVLSPRQLQ LSMCVGECPH

51  LYRSANTHAQ IKARLHGLQP DKVPAPCCVP SSYTPVVLMH RTDSGVSLQT

101  YDDLVARGCH CA
```

An N'Δ4 truncated variant of mature mouse GDF15 (SEQ ID NO: 12) corresponding to amino acids 196-303 of SEQ ID NO: 10.

```
                                                      (SEQ ID NO: 12)
  1   DSCPLGPGRC  CHLETVQATL  EDLGWSDWVL  SPRQLQLSMC  VGECPHLYRS

51   ANTHAQIKAR  LHGLQPDKVP  APCCVPSSYT  PVVLMHRTDS  GVSLQTYDDL

101   VARGCHCA
```

In certain aspects, functional variants or modified forms of GDF15 polypeptides include fusion proteins having at least a portion of the GDF15 polypeptide and one or more fusion domains. Well-known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with fusion parters containing a $His_6$ tag (SEQ ID NO: 15).

As another example, a fusion domain may be selected so as to facilitate detection of the GDF15 polypeptides. Examples of such detection domains include the various fluorescent proteins (e.g., GFP) as well as "epitope tags," which are usually short peptide sequences for which a specific antibody is available. Well-known epitope tags for which specific monoclonal antibodies are readily available include FLAG, influenza virus haemagglutinin (HA), and c-myc tags. In some cases, the fusion domains have a protease cleavage site, such as for factor Xa or thrombin, which allows the relevant protease to partially digest the fusion proteins and thereby liberate the recombinant proteins therefrom. The liberated proteins can then be isolated from the fusion domain by subsequent chromatographic separation.

In certain preferred embodiments, a GDF15 polypeptide is fused with a domain that stabilizes the GDF15 polypeptide in vivo (a "stabilizer" domain). By "stabilizing" is meant anything that increases serum half life, regardless of whether this is because of decreased destruction, decreased clearance by the kidney, or other pharmacokinetic effects. Fusions with the Fc portion of an immunoglobulin are known to confer desirable pharmacokinetic properties on a wide range of proteins. Likewise, fusions to human serum albumin can confer desirable properties. Other types of fusion domains that may be selected include multimerizing (e.g., dimerizing, tetramerizing) stabilizing domains or functional domains. For example, GDF15 polypeptide fusion proteins may be designed as heteromeric structures as disclosed in PCT Publication Nos. WO 2013/113008 and WO 2014/100689.

As used herein, the term "immunoglobulin Fc domain" or simply "Fc" is understood to mean the carboxyl-terminal portion of an immunoglobulin chain constant region, preferably an immunoglobulin heavy chain constant region, or a portion thereof. For example, an immunoglobulin Fc region may comprise 1) a CH1 domain, a CH2 domain, and a CH3 domain, 2) a CH1 domain and a CH2 domain, 3) a CH1 domain and a CH3 domain, 4) a CH2 domain and a CH3 domain, or 5) a combination of two or more domains and an immunoglobulin hinge region. In certain embodiments the immunoglobulin Fc region comprises at least an immunoglobulin hinge region, a CH2 domain, and a CH3 domain, and preferably lacks the CH1 domain.

In one embodiment, the class of immunoglobulin from which the heavy chain constant region is derived is IgG (Igγ) (γ subclasses 1, 2, 3, or 4). Examples of GDF15 polypeptide fusion proteins comprising IgG Fc are disclosed in PCT Publication Nos. WO 2013/113008 and WO 2014/100689. Other classes of immunoglobulin, IgA (Igα), IgD (Igδ), IgE (Igε) and IgM (Igμ), may be used. The choice of appropriate immunoglobulin heavy chain constant region is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fc gamma or the homologous domains in any of IgA, IgD, IgE, or IgM.

Furthermore, it is contemplated that substitution or deletion of amino acids within the immunoglobulin heavy chain constant regions may be useful in the practice of the methods and compositions disclosed herein. See, for example, PCT Publication No. WO 2013/113008. Optionally, the Fc domain has one or more mutations which confer reduced ability of binding to the Fcγ receptor relative to a wildtype Fc domain. In other cases, the mutant Fc domain has one or more mutations which confer increased ability of binding to the MHC class I-related Fc-receptor (FcRN) relative to a wildtype Fc domain.

It is understood that different elements of the fusion proteins may be arranged in any manner that is consistent with the desired functionality. For example, a GDF15 polypeptide may be placed C-terminal to a heterologous domain, or, alternatively, a heterologous domain may be placed C-terminal to a GDF15 polypeptide. The GDF15 polypeptide domain and the heterologous domain need not be adjacent in a fusion protein, and additional domains or amino acid sequences may be included C- or N-terminal to either domain or between the domains.

In certain aspects, the disclosure provides isolated and/or recombinant nucleic acids encoding any of the GDF15 polypeptides disclosed herein. Such nucleic acids may be DNA or RNA molecules. These nucleic acids may be used, for example, in methods for making GDF15 polypeptides or as direct therapeutic agents (e.g., in a gene therapy approach).

A nucleic acid sequence encoding native human GDF15 precursor protein is as follows (SEQ ID NO: 13). The leader sequence is encoded by nucleotides 1-87, the prodomain by nucleotides 88-588, and mature GDF15 by nucleotides 589-924).

(SEQ ID NO: 13)
```
  1 ATGCCCGGGC AAGAACTCAG GACGGTGAAT GGCTCTCAGA TGCTCCTGGT

51 GTTGCTGGTG CTCTCGTGGC TGCCGCATGG GGGCGCCCTG TCTCTGGCCG

101 AGGCGAGCCG CGCAAGTTTC CCGGGACCCT CAGAGTTGCA CTCCGAAGAC

151 TCCAGATTCC GAGAGTTGCG GAAACGCTAC GAGGACCTGC TAACCAGGCT

201 GCGGGCCAAC CAGAGCTGGG AAGATTCGAA CACCGACCTC GTCCCGGCCC

251 CTGCAGTCCG GATACTCACG CCAGAAGTGC GGCTGGGATC CGGCGGCCAC

301 CTGCACCTGC GTATCTCTCG GGCCGCCCTT CCCGAGGGGC TCCCCGAGGC

351 CTCCCGCCTT CACCGGGCTC TGTTCCGGCT GTCCCCGACG GCGTCAAGGT

401 CGTGGGACGT GACACGACCG CTGCGGCGTC AGCTCAGCCT TGCAAGACCC

451 CAGGCACCCG CGCTGCACCT GCGACTGTCG CCGCCGCCGT CGCAGTCGGA

501 CCAACTGCTG GCAGAATCTT CGTCCGCACG GCCCCAGCTG GAGTTGCACT

551 TGCGGCCGCA AGCCGCCAGG GGGCGCCGCA GAGCGCGTGC GCGCAACGGG

601 GACCACTGTC CGCTCGGGCC CGGGCGTTGC TGCCGTCTGC ACACGGTCCG

651 CGCGTCGCTG GAAGACCTGG GCTGGGCCGA TTGGGTGCTG TCGCCACGGG

701 AGGTGCAAGT GACCATGTGC ATCGGCGCGT GCCCGAGCCA GTTCCGGGCG

751 GCAAACATGC ACGCGCAGAT CAAGACGAGC CTGCACCGCC TGAAGCCCGA

801 CACGGTGCCA GCGCCCTGCT GCGTGCCCGC CAGCTACAAT CCCATGGTGC

851 TCATTCAAAA GACCGACACC GGGGTGTCAC TCCAGACCTA TGATGACTTG

901 TTAGCCAAAG ACTGCCACTG CATA
```

A nucleic acid sequence (positions 24-932 of NCBI Reference Sequence No. NM_011819.2) encoding native mouse GDF15 precursor protein is as follows (SEQ ID NO: 14). The leader sequence is encoded by nucleotides 1-90, the prodomain by nucleotides 91-573, and mature GDF15 by nucleotides 574-909).

(SEQ ID NO: 14)
```
  1 ATGGCCCCGC CCGCGCTCCA GGCCCAGCCT CCAGGCGGCT CTCAACTGAG

51 GTTCCTGCTG TTCCTGCTGC TGTTGCTGCT GCTGCTGTCA TGGCCATCGC

101 AGGGGGACGC CCTGGCAATG CCTGAACAGC GACCCTCCGG CCCTGAGTCC

151 CAACTCAACG CCGACGAGCT ACGGGGTCGC TTCCAGGACC TGCTGAGCCG

201 GCTGCATGCC AACCAGAGCC GAGAGGACTC GAACTCAGAA CCAAGTCCTG

251 ACCCAGCTGT CCGGATACTC AGTCCAGAGG TGAGATTGGG GTCCCACGGC

301 CAGCTGCTAC TCCGCGTCAA CCGGGCGTCG CTGAGTCAGG GTCTCCCCGA

351 AGCCTACCGC GTGCACCGAG CGCTGCTCCT GCTGACGCCG ACGGCCCGCC

401 CCTGGGACAT CACTAGGCCC CTGAAGCGTG CGCTCAGCCT CCGGGGACCC

451 CGTGCTCCCG CATTACGCCT GCGCCTGACG CCGCCTCCGG ACCTGGCTAT

501 GCTGCCCTCT GGCGGCACGC AGCTGGAACT GCGCTTACGG GTAGCCGCCG

551 GCAGGGGGCG CCGAAGCGCG CATGCGCACC CAAGAGACTC GTGCCCACTG

601 GGTCCAGGGC GCTGCTGTCA CTTGGAGACT GTGCAGGCAA CTCTTGAAGA

651 CTTGGGCTGG AGCGACTGGG TGCTGTCCCC GCGCCAGCTG CAGCTGAGCA

701 TGTGCGTGGG CGAGTGTCCC CACCTGTATC GCTCCGCGAA CACGCATGCG

751 CAGATCAAAG CACGCCTGCA TGGCCTGCAG CCTGACAAGG TGCCTGCCCC
```

```
801 GTGCTGTGTC CCCTCCAGCT ACACCCCGGT GGTTCTTATG CACAGGACAG

851 ACAGTGGTGT GTCACTGCAG ACTTATGATG ACCTGGTGGC CCGGGGCTGC

901 CACTGCGCT
```

In certain aspects, the subject nucleic acids encoding GDF15 polypeptides are further understood to include nucleic acids that are variants of SEQ ID NO: 13 Variant nucleotide sequences include sequences that differ by one or more nucleotide substitutions, additions or deletions, such as allelic variants; and will, therefore, include coding sequences that differ from the nucleotide sequence of the coding sequence designated in SEQ ID NO: 13.

In certain embodiments, the disclosure provides isolated or recombinant nucleic acid sequences that are at least 68%, 70%, 80%, 85%, 90%, 95%, 97%, 98%, 99% or 100% identical to SEQ ID NO: 13 or the portions thereof that encode the prodomain or mature portion. One of ordinary skill in the art will appreciate that nucleic acid sequences complementary to SEQ ID NO: 13, and variants of SEQ ID NO: 13, are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences that hybridize under stringent conditions to the nucleotide sequence designated in SEQ ID NO: 13, including the portions thereof that encode the prodomain or mature portion, complement sequence of SEQ ID NO: 13, including the portions thereof that encode the prodomain or mature portion thereof. In a particular embodiment, the disclosure provides nucleic acids that hybridize under stringent conditions to a complement of the nucleic acid of 589-924 of SEQ ID NO: 13, and GDF15 polypeptides encoded by the foregoing. As discussed above, one of ordinary skill in the art will understand readily that appropriate stringency conditions which promote DNA hybridization can be varied. For example, one could perform the hybridization at 6.0×sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by a wash at 2×SSC at room temperature.

Isolated nucleic acids which differ from the nucleic acids as set forth in SEQ ID NO: 13 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. In certain embodiments, the GDF15 polypeptide will be encoded by an alternative nucleotide sequence. Alternative nucleotide sequences are degenerate with respect to the native GDF15 nucleic acid sequence but still encode the same protein.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the disclosure, the subject nucleic acid is provided in an expression vector comprising a nucleotide sequence encoding a GDF15 polypeptide and operably linked to at least one regulatory sequence. Regulatory sequences are art-recognized and are selected to direct expression of the GDF15 polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding a GDF15 polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid for production of GDF15 polypeptides can be produced by ligating the cloned gene, or a portion thereof, into a vector suitable for expression in either prokaryotic cells, eukaryotic cells (yeast, avian, insect or mammalian), or both. Expression vehicles for production of recombinant GDF15 polypeptides include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as E. coli.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the *bovine papilloma virus (BPV-*1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual,* 2nd Ed., ed. by Sambrook, Fritsch and Maniatis (Cold Spring Harbor Laboratory Press, 1989) Chapters 16 and 17. In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject GDF15 polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject GDF15 polypeptides in cells propagated in culture, e.g., to produce proteins, including fusion proteins or variant proteins, for purification.

This disclosure also pertains to a host cell transfected with a recombinant gene including a coding sequence for one or more of the subject GDF15 polypeptides. The host cell may be any prokaryotic or eukaryotic cell. For example, a GDF15 polypeptide of the invention may be expressed in bacterial cells such as *E. coli,* insect cells (e.g., using a baculovirus expression system), yeast, or mammalian cells. Other suitable host cells are known to those skilled in the art.

The above-described nucleic acids may be used to express GDF15 polypeptides in suitable cells, including, for example, HEK cells, COS cells and CHO cells. The signal sequence can be a native signal sequence of GDF15, or a signal sequence from another protein, such as a tissue plasminogen activator (TPA) signal sequence or a honey bee melittin (HBM) signal sequence. The protein PACE (or furin) mediates cleavage of the proprotein into two peptides, the proprotein and the mature portion, and thus it is useful to express a PACE transgene in a cell that is intended to produce a GDF15 polypeptide if such cleavage is desired. It is generally accepted that members of the GDF or BMP families need to dissociate from their prodomains in order to become fully active. In the case of GDF15, the prodomain separates from the mature portion under native conditions but may first assist in proper generation of the bioactive, administrable pharmaceutical form. Alternatively, it is recognized here that the prodomain may confer desirable pharmaceutical properties, including, for example, longer serum half-life and greater bioavailability, and thus in certain embodiments the disclosure provides pharmaceutical preparations comprising the mature portion of a GDF15 polypeptide that is covalently or non-covalently associated with a prodomain polypeptide. A "prodomain polypeptide" is a polypeptide comprising, consisting essentially of, or consisting of, an amino acid sequence that is at least 68%, 70%, 75%, 80%, 85%, 90%, 95%, 97%, 98%, 99%, or 100% identical to the sequence of a naturally occurring GDF15 prodomain such as amino acids 30-196 of SEQ ID NO: 1. It will be apparent that a prodomain polypeptide should not generally include more than 30, 20, 10 or 5 amino acids of the corresponding mature portion. In certain embodiments, a prodomain polypeptide will bind to the mature portion of a GDF15 polypeptide with a $K_D$ of no greater than $10^{-6}$ M, $10^{-7}$ M, $10^{-8}$ M or $10^{-9}$ M, or less.

In certain embodiments, the present disclosure contemplates making functional variants by modifying the structure of a GDF15 polypeptide for such purposes as enhancing therapeutic efficacy, or stability (e.g., ex vivo shelf life and resistance to proteolytic degradation in vivo). GDF15 polypeptides can also be generated by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of a GDF15 polypeptide results in a functional variant can be readily determined by assessing the ability of the variant GDF15 polypeptide to produce a response in cells relative to the unmodified GDF15 polypeptide, or to bind to one or more receptors. In the case of variations in a prodomain polypeptide, the functional activity of a variant may be assessed by measuring the ability of the prodomain to bind to a mature GDF15 polypeptide.

In certain embodiments, the present invention contemplates GDF15 polypeptides having specific mutations so as to alter the glycosylation of the GDF15 polypeptide. Alterations in amino acid sequence may be made so as to introduce one or more N-linked glycosylation sites, which are generally an NXS or NXT sequence. Mutations may also be selected so as to eliminate one or more glycosylation sites, such as O-linked or N-linked glycosylation sites. The alteration may also be made by the addition of, or substitution by, one or more asparagine, serine or threonine residues to the sequence of a GDF15 polypeptide. A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a GDF15 polypeptide is by chemical or enzymatic coupling of glycosides to the GDF15 polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. These methods are described in WO 87/05330 and in Aplin and Wriston (1981) CRC Crit. Rev. Biochem., pp. 259-306, incorporated by reference herein. Removal of one or more carbohydrate moieties present on a GDF15 polypeptide may be accomplished chemically and/or enzymatically. Chemical deglycosylation may involve, for example, exposure of the GDF15 polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Chemical deglycosylation is further described by Hakimuddin et al. (1987) Arch. Biochem. Biophys. 259:52 and by Edge et al. (1981) Anal. Biochem. 118:131. Enzymatic cleavage of carbohydrate moieties on GDF15 polypeptides can be achieved by the use of a variety of endo- and exo-glycosidases as described by Thotakura et al. (1987) Meth. Enzymol. 138:350. The sequence of a GDF15 polypeptide may be adjusted, as appropriate, depending on the type of expression system used, as mammalian, yeast, insect and plant cells may all introduce differing glycosylation patterns that can be affected by the amino acid sequence of the peptide. In general, GDF15 polypeptides for use in humans will be expressed in a mammalian cell line that provides proper glycosylation, such as HEK293 or CHO cell lines, although other mammalian expression cell lines are expected to be useful as well.

This disclosure further contemplates a method of generating variants, particularly sets of combinatorial variants of a GDF15 polypeptide, including, optionally, truncation variants; pools of combinatorial mutants are especially useful for identifying GDF15 sequences. The purpose of screening such combinatorial libraries may be to generate, for example, GDF15 polypeptide variants which have altered properties, such as altered pharmacokinetics, or altered receptor binding. A variety of screening assays are provided below, and such assays may be used to evaluate variants.

The activity of a GDF15 polypeptide or its variants may also be tested in a cell-based or in vivo assay. For example, the effect of a GDF15 polypeptide variant on the expression of genes involved in hematopoiesis may be assessed. Likewise, a GDF15 polypeptide may be administered to a mouse or other animal, and one or more blood measurements, such as red blood cell count, hemoglobin levels, hematocrit levels, iron stores, or reticulocyte count may be assessed using art-recognized methods. Bioactivity of GDF15 and other ligands that stimulate SMAD2/3 signaling can be assessed in A549 cells (a human pulmonary epithelial cell line) transfected with a reporter gene containing a CAGA-12 promoter construct. This construct incorporates multiple repeats of a SMAD2/3-binding motif originally identified in the promoter region of the human PAI-1 gene (Dennler et al., 1998, EMBO J 17:3091-3100). See U.S. patent application Ser. No. 14/465,182. Bioactivity of GDF15 polypeptide may also be assessed by inhibition of growth by DU-145 cells.

In certain embodiments, the GDF15 polypeptides may further comprise post-translational modifications in addition to any that are naturally present in the GDF15 polypeptides. Such modifications include, but are not limited to, acetylation, carboxylation, glycosylation, phosphorylation, lipidation, acylation and modification with polyethylene glycol (PEG). As a result, GDF15 polypeptides may contain non-amino acid elements, such as polyethylene glycols, lipids, poly- or mono-saccharide, and phosphates. Effects of such non-amino acid elements on the functionality of a GDF15 polypeptide may be tested as described herein for other GDF15 polypeptide variants. When a GDF15 polypeptide is produced in cells by cleaving a nascent form of GDF15 polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the GDF15 polypeptides.

In certain embodiments, the present invention makes available isolated and/or purified forms of the GDF15 polypeptides, which are isolated from, or otherwise substantially free of, other proteins.

In certain embodiments, GDF15 polypeptides (unmodified or modified) of the invention can be produced by a variety of art-known techniques. For example, polypeptides can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the GDF15 polypeptides, fragments or variants thereof may be recombinantly produced using various expression systems (e.g., E. coli, Chinese hamster ovary (CHO) cells, COS cells, baculovirus) as is well known in the art, followed by protein purification.

Accordingly, the disclosure provides methods of producing the subject GDF15 polypeptides. For example, a host cell transfected with an expression vector encoding a GDF15 polypeptide can be cultured under appropriate conditions to allow expression of the polypeptide to occur. The GDF15 polypeptide may be secreted and isolated from a mixture of cells and medium containing the GDF15 polypeptide. Alternatively, the polypeptide may be retained cytoplasmically or in a membrane fraction and the cells harvested, lysed and the protein isolated. A cell culture includes host cells, media and other byproducts. Suitable media for cell culture are well known in the art. The subject GDF15 polypeptides can be isolated from cell culture medium, host cells, or both, using techniques known in the art for purifying proteins, including ion-exchange chromatography, gel filtration chromatography, ultrafiltration, electrophoresis, and immunoaffinity purification with antibodies specific for particular epitopes of the GDF15 polypeptides.

The disclosure further provides novel methods for purification of GDF15 polypeptides. In one embodiment, GDF15 polypeptides can be purified with a cation-exchange column using high concentrations of urea for elution, for example, a urea concentration of 4 M, 5 M, 6 M, 7 M, or 8 M. In another embodiment, GDF15 polypeptides can be purified with an anion-exchange column. In yet another embodiment, GDF15 polypeptides can be purified with a reverse-phase HPLC column. Cation exchange with urea elution, anion exchange, and reverse-phase HPLC can be performed in any order. In a preferred embodiment, GDF15 polypeptides can be purified first with cation exchange and elution with urea, second with anion exchange, and third with a reverse-phase HPLC column.

A solid matrix (e.g., chromatography resin) may be joined to a ligand-binding portion of any of the foregoing to create an affinity matrix that will bind selectively to GDF15 polypeptides. The extracellular domain of the receptor may be fused to an Fc portion of an immunoglobulin and joined to a matrix containing an Fc binding protein, such as protein A.

In another embodiment, a fusion gene coding for a purification leader sequence, such as a poly-(His)/enterokinase cleavage site sequence at the N-terminus of the desired portion of the recombinant GDF15 polypeptide, can allow purification of the expressed fusion protein by affinity chromatography using a $Ni^{2+}$ metal resin. The purification leader sequence can then be subsequently removed by treatment with enterokinase to provide the purified GDF15 polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

3. Exemplary Therapeutic Uses

In certain embodiments, GDF15 polypeptides of the present disclosure can be used to increase red blood cell levels in mammals such as rodents and primates, and particularly human patients. Additionally, GDF15 polypeptides may be used in combination with EPO receptor activators to achieve an increase in red blood cells at lower dose ranges or to achieve an overall higher level of red blood cells or a greater response rate. This may be beneficial in reducing the known off-target effects and risks associated with high doses of EPO receptor activators. In certain embodiments, the present invention provides methods of treating or preventing anemia in an individual in need thereof by administering to the individual a therapeutically effective amount of a GDF15 polypeptide or a combination (or concomitant therapy) of a GDF15 polypeptide and a EPO receptor activator. These methods may be used for therapeutic and prophylactic treatments of mammals, and particularly humans.

The GDF15 polypeptides may be used in combination with EPO receptor activators to reduce the required dose of these activators in patients that are susceptible to adverse effects of EPO. The primary adverse effects of EPO are an excessive increase in the hematocrit or hemoglobin levels and polycythemia. Elevated hematocrit levels can lead to hypertension (more particularly aggravation of hypertension) and vascular thrombosis. Other adverse effects of EPO which have been reported, some of which related to hypertension, are headaches, influenza-like syndrome, obstruction of shunts, myocardial infarctions and cerebral convulsions due to thrombosis, hypertensive encephalopathy, and red cell blood cell applasia (Singibarti, 1994, J. Clin Invest 72(suppl 6):S36-S43; Horl et al., 2000, Nephrol Dial Transplant 15(suppl 4):51-56; Delanty et al., 1997, Neurology 49:686-689; Bunn, 2002, N Engl J Med 346:522-523).

The synergistic effect of a GDF15 polypeptide and EPO on hemoglobin concentrations as disclosed herein indicates that GDF15 polypeptides act by a mechanism different from that of EPO. Accordingly, these antagonists may be useful for increasing red blood cell and hemoglobin levels in patients that do not respond well to EPO. For example, a GDF15 polypeptide may be beneficial for a patient in which administration of a normal-to-increased dose of EPO (>300 IU/kg/week) does not increase hemoglobin concentrations to the target level. Patients with an inadequate EPO response are found for all types of anemia, but higher numbers of non-responders have been observed particularly frequently in patients with cancers and patients with end-stage renal disease. An inadequate response to EPO can be either constitutive (i.e. observed upon the first treatment with EPO) or acquired (e.g. observed upon repeated treatment with EPO).

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes prophylaxis of the named condition or amelioration or elimination of the condition once it has been established. In either case, prevention or treatment may be discerned in the diagnosis provided by a physician or other health care provider and the intended result of administration of the therapeutic agent.

As shown herein, GDF15 polypeptides, optionally combined with an EPO receptor activator, may be used to increase red blood cell, hemoglobin, or reticulocyte levels in healthy individuals, and such GDF15 polypeptides may be used in selected patient populations. Examples of appropriate patient populations include those with undesirably low red blood cell or hemoglobin levels, such as patients having an anemia, and those that are at risk for developing undesirably low red blood cell or hemoglobin levels, such as those patients that are about to undergo major surgery or other procedures that may result in substantial blood loss. In one embodiment, a patient with adequate red blood cell levels is treated with a GDF15 polypeptide to increase red blood cell levels, and then blood is drawn and stored for later use in transfusions.

GDF15 polypeptides disclosed herein, optionally combined with an EPO receptor activator, may be used to increase red blood cell levels in patients having an anemia. When observing hemoglobin levels in humans, a level of less than normal for the appropriate age and gender category may be indicative of anemia, although individual variations are taken into account. For example, a hemoglobin level of 12 g/dl is generally considered the lower limit of normal in the general adult population. Potential causes for hemoglobin insufficiency include blood loss, nutritional deficits, reactions to medication, various disorders of the bone marrow, and many diseases. More particularly, anemia has been associated with a variety of disorders that include, for example, chronic renal failure, myelodysplastic syndrome, rheumatoid arthritis, and bone marrow transplantation. Anemia may also be associated with the following conditions: solid tumors (e.g. breast cancer, lung cancer, colon cancer); tumors of the lymphatic system (e.g. chronic lymphocyte leukemia, non-Hodgkins and Hodgkins lymphomas); tumors of the hematopoietic system (e.g. leukemia, myelodysplastic syndrome, multiple myeloma); radiation therapy; chemotherapy (e.g. platinum containing regimens); inflammatory and autoimmune diseases, including, but not limited to, rheumatoid arthritis, other inflammatory arthritides, systemic lupus erythematosis (SLE), acute or chronic skin diseases (e.g. psoriasis), inflammatory bowel disease (e.g. Crohn's disease and ulcerative colitis); acute or chronic renal disease or failure including idiopathic or congenital conditions; acute or chronic liver disease; acute or chronic bleeding; situations where transfusion of red blood cells is not possible due to patient allo- or auto-antibodies and/or for religious reasons (e.g. some Jehovah's Witnesses); infections (e.g. malaria, osteomyelitis); hemoglobinopathies, including, for example, sickle cell disease, thalassemias; drug use or abuse, e.g. alcohol misuse; pediatric patients with anemia from any cause to avoid transfusion; and elderly patients or patients with underlying cardiopulmonary disease with anemia who cannot receive transfusions due to concerns about circulatory overload.

The most common type of anemia is anemia of chronic disease, which encompasses inflammation, infection, tissue injury, and conditions such as cancer. Anemia of chronic disease is distinguished by both low EPO levels and an inadequate response to EPO in the bone marrow (Adamson, 2008, Harrison's Principles of Internal Medicine, 17th ed.; McGraw Hill, New York, pp 628-634). Many factors can contribute to cancer-related anemia. Some are associated with the disease process itself and the generation of inflammatory cytokines such as interleukin-1, interferon-gamma, and tumor necrosis factor (Bron et al., 2001, Semin Oncol 28(Suppl 8):1-6). Among its effects, inflammation induces the key iron-regulatory peptide hepcidin, thereby inhibiting iron export from macrophages and generally limiting iron availability for erythropoiesis (Ganz, 2007, J Am Soc Nephrol 18:394-400). Blood loss through various routes can also contribute to cancer-related anemia. The prevalence of anemia due to cancer progression varies with cancer type, ranging from 5% in prostate cancer up to 90% in multiple myeloma. Cancer-related anemia has profound consequences for patients, including fatigue and reduced quality of life, reduced treatment efficacy, and increased mortality.

Chronic kidney disease is associated with hypoproliferative anemia that varies in severity with the degree of renal impairment. Such anemia is primarily due to inadequate production of EPO and reduced survival of red blood cells. Chronic kidney disease usually proceeds gradually over a period of years or decades to end-stage (Stage-5) disease, at which point dialysis or kidney transplantation is required for patient survival. Anemia often develops early in this process and worsens as disease progresses. The clinical consequences of anemia of kidney disease are well-documented and include development of left ventricular hypertrophy, impaired cognitive function, reduced quality of life, and altered immune function (Levin et al., 1999, Am J Kidney Dis 27:347-354; Nissenson, 1992, Am J Kidney Dis 20(Suppl 1):21-24; Revicki et al., 1995, Am J Kidney Dis 25:548-554; Gafter et al., 1994, Kidney Int 45:224-231). A GDF15 polypeptide, optionally combined with an EPO receptor activator, can be used to treat anemia of kidney disease.

Many conditions resulting in a hypometabolic rate can produce a mild-to-moderate hypoproliferative anemia. Among such conditions are endocrine deficiency states. For example, anemia can occur in Addison's disease, hypothyroidism, hyperparathyroidism, or males who are castrated or treated with estrogen. Mild-to-moderate anemia can also occur with reduced dietary intake of protein, a condition particularly prevalent in the elderly. Finally, anemia can develop in patients with chronic liver disease arising from nearly any cause (Adamson, 2008, Harrison's Principles of Internal Medicine, 17th ed.; McGraw Hill, New York, pp 628-634).

Anemia resulting from acute blood loss of sufficient volume, such as from trauma or postpartum hemorrhage, is known as acute post-hemorrhagic anemia. Acute blood loss initially causes hypovolemia without anemia since there is proportional depletion of red blood cells along with other blood constituents. However, hypovolemia will rapidly trigger physiologic mechanisms that shift fluid from the extravascular to the vascular compartment, which results in hemodilution and anemia. If chronic, blood loss gradually depletes body iron stores and eventually leads to iron deficiency. Results disclosed herein implicate GDF15 as an endogenous erythropoietic signal triggered by acute blood-loss anemia to promote red blood cell production. Therefore, a GDF15 polypeptide, optionally combined with an EPO receptor activator, can be used to speed recovery from anemia of acute blood loss.

Iron-deficiency anemia is the final stage in a graded progression of increasing iron deficiency which includes negative iron balance and iron-deficient erythropoiesis as intermediate stages. Iron deficiency can result from increased iron demand, decreased iron intake, or increased iron loss, as exemplified in conditions such as pregnancy, inadequate diet, intestinal malabsorption, acute or chronic inflammation, and acute or chronic blood loss. With mild-to-moderate anemia of this type, the bone marrow remains hypoproliferative, and red blood cell morphology is largely normal; however, even mild anemia can result in some microcytic hypochromic red blood cells, and the transition to severe iron-deficient anemia is accompanied by hyperproliferation of the bone marrow and increasingly prevalent microcytic and hypochromic red blood cells (Adamson, 2008, Harrison's Principles of Internal Medicine, 17th ed.; McGraw Hill, New York, pp 628-634). Appropriate therapy for iron-deficiency anemia depends on its cause and severity, with oral iron preparations, parenteral iron formulations, and transfusion of red blood cells as major conventional options. A GDF15 polypeptide, optionally combined with an EPO receptor activator, could be used to treat chronic iron-deficiency anemias alone or in combination with conventional therapeutic approaches, particularly to treat anemias of multifactorial origin.

GDF15 polypeptides, optionally combined with an EPO receptor activator, would be appropriate for treating anemias of hypoproliferative bone marrow, which are typically associated with little change in red blood cell morphology. Hypoproliferative anemias include: 1) anemia of chronic disease, 2) anemia of kidney disease, and 3) anemia associated with hypometabolic states. In each of these types, endogenous EPO levels are inappropriately low for the degree of anemia observed. Other hypoproliferative anemias include: 4) early-stage iron-deficient anemia, and 5) anemia caused by damage to the bone marrow. In these types, endogenous EPO levels are appropriately elevated for the degree of anemia observed. Hypoproliferative anemias also can result myelosuppression caused by cancer chemotherapeutic drugs or cancer radiation therapy. A broad review of clinical trials found that mild anemia can occur in 100% of patients after chemotherapy, while more severe anemia can occur in up to 80% of such patients (Groopman et al., 1999, J Natl Cancer Inst 91:1616-1634). Myelosuppressive drugs include: 1) alkylating agents such as nitrogen mustards (e.g., melphalan) and nitrosoureas (e.g., streptozocin); 2) antimetabolites such as folic acid antagonists (e.g., methotrexate), purine analogs (e.g., thioguanine), and pyrimidine analogs (e.g., gemcitabine); 3) cytotoxic antibiotics such as anthracyclines (e.g., doxorubicin); 4) kinase inhibitors (e.g., gefitinib); 5) mitotic inhibitors such as taxanes (e.g., paclitaxel) and vinca alkaloids (e.g., vinorelbine); 6) monoclonal antibodies (e.g., rituximab); and 7) topoisomerase inhibitors (e.g., topotecan and etoposide). A GDF15 polypeptide, optionally combined with an EPO receptor activator, can be used to treat anemia caused by chemotherapeutic agents and/or radiation therapy.

In some embodiments, GDF15 polypeptides, optionally combined with an EPO receptor activator, would also be appropriate for treating anemias of disordered red blood cell maturation, which are characterized in part by undersized (microcytic), oversized (macrocytic), misshapen, or abnormally colored (hypochromic) red blood cells.

In certain embodiments, an GDF15 polypeptide, optionally combined with an EPO receptor activator, can be useful for treating ineffective erythropoiesis. Originally distinguished from aplastic anemia, hemorrhage, or peripheral hemolysis on the basis of ferrokinetic studies (Ricketts et al., 1978, Clin Nucl Med 3:159-164), ineffective erythropoiesis describes a diverse group of anemias in which production of mature RBCs is less than would be expected given the number of erythroid precursors (erythroblasts) present in the bone marrow (Tanno et al., 2010, Adv Hematol 2010: 358283). In such anemias, tissue hypoxia persists despite elevated erythropoietin levels due to ineffective production of mature RBCs. A vicious cycle eventually develops in which elevated erythropoietin levels drive massive expansion of erythroblasts, potentially leading to splenomegaly (spleen enlargement) due to extramedullary erythropoiesis (Aizawa et al, 2003, Am J Hematol 74:68-72), erythroblast-induced bone pathology (Di Matteo et al, 2008, J Biol Regul Homeost Agents 22:211-216), and tissue iron overload, even in the absence of therapeutic RBC transfusions (Pippard et al, 1979, Lancet 2:819-821). Thus, by boosting erythropoietic effectiveness, a GDF15 polypeptide may break the aforementioned cycle and may alleviate not only the underlying anemia but also the associated complications of elevated erythropoietin levels, splenomegaly, bone pathology, and tissue iron overload. GDF15 polypeptides can treat ineffective erythropoiesis, including anemia and elevated EPO levels, as well as complications such as splenomegaly, erythroblast-induced bone pathology, and iron overload, and their attendant pathologies. With splenomegaly, such pathologies include thoracic or abdominal pain and reticuloendothelial hyperplasia. Extramedullary hematopoiesis can occur not only in the spleen but potentially in other tissues in the form of extramedullary hematopoietic pseudotumors (Musallam et al., 2012, Cold Spring Harb Perspect Med 2:a013482). With erythroblast-induced bone pathology, attendant pathologies include low bone mineral density, osteoporosis, and bone pain (Haidar et al., 2011, Bone 48:425-432). With iron overload, attendant pathologies include hepcidin suppression and hyperabsorption of dietary iron (Musallam et al., 2012, Blood Rev 26(Suppl 1):S16-S19), multiple endocrinopathies and liver fibrosis/cirrhosis (Galanello et al., 2010, Orphanet J Rare Dis 5:11), and iron-overload cardiomyopathy (Lekawanvijit et al., 2009, Can J Cardiol 25:213-218).

The most common causes of ineffective erythropoiesis are the thalassemia syndromes, hereditary hemoglobinopathies in which imbalances in the production of intact alpha- and beta-hemoglobin chains lead to increased apoptosis during erythroblast maturation (Schrier, 2002, Curr Opin Hematol 9:123-126). Thalassemias are collectively among the most frequent genetic disorders worldwide, with changing epidemiologic patterns predicted to contribute to a growing public health problem in both the U.S. and globally (Vichinsky, 2005, Ann NY Acad Sci 1054:18-24). Thalassemia syndromes are named according to their severity. Thus, α-thalassemias include α-thalassemia minor (also known as α-thalassemia trait; two affected α-globin genes), hemoglobin H disease (three affected α-globin genes), and α-thalassemia major (also known as hydrops fetalis; four affected α-globin genes). β-Thalassemias include β-thalassemia minor (also known as β-thalassemia trait; one affected β-globin gene), β-thalassemia intermedia (two affected β-globin genes), hemoglobin E thalassemia (two affected β-globin genes), and β-thalassemia major (also known as Cooley's anemia; two affected β-globin genes resulting in a complete absence of β-globin protein). β-Thalassemia impacts multiple organs, is associated with considerable morbidity and mortality, and currently requires life-long care. Although life expectancy in patients with β-thalassemia has increased in recent years due to use of regular blood transfusions in combination with iron chelation, iron overload resulting both from transfusions and from excessive gastrointestinal absorption of iron can cause serious complications such as heart disease, thrombosis, hypogonadism, hypothyroidism, diabetes, osteoporosis, and osteopenia (Rund et al, 2005, N Engl J Med 353:1135-1146). As demonstrated herein with a mouse model of β-thalassemia, a GDF15 polypeptide, optionally combined with an EPO receptor activator, can be used to treat thalassemia syndromes such as those described herein.

In some embodiments, GDF15 polypeptides, optionally combined with an EPO receptor activator, can be used for treating disorders of ineffective erythropoiesis besides thalassemia syndromes. Such disorders include siderblastic anemia (inherited or acquired); dyserythropoietic anemia (Types I and II); sickle cell anemia; hereditary spherocytosis; pyruvate kinase deficiency; megaloblastic anemias, potentially caused by conditions such as folate deficiency (due to congenital diseases, decreased intake, or increased requirements), cobalamin deficiency (due to congenital diseases, pernicious anemia, impaired absorption, pancreatic insufficiency, or decreased intake), certain drugs, or unexplained causes (congenital dyserythropoietic anemia, refractory megaloblastic anemia, or erythroleukemia); myelophthisic anemias, including myelofibrosis (myeloid metaplasia) and myelophthisis; congenital erythropoietic porphyria; and lead poisoning.

In certain embodiments, GDF15 polypeptides may be used in combination (e.g., administered at the same time or different times, but generally in such a manner as to achieve overlapping pharmacologic effects) with supportive therapies for ineffective erythropoiesis. Such therapies include transfusion with either red blood cells or whole blood to treat anemia. In chronic or hereditary anemias, normal mechanisms for iron homeostasis are overwhelmed by repeated transfusions, eventually leading to toxic and potentially fatal accumulation of iron in vital tissues such as heart, liver, and endocrine glands. Thus, supportive therapies for patients chronically afflicted with ineffective erythropoiesis also include treatment with one or more iron-chelating molecules to promote iron excretion in the urine and/or stool and thereby prevent, or reverse, tissue iron overload (Hershko, 2006, Haematologica 91:1307-1312; Cao et al, 2011, Pediatr Rep 3(2):e17). Effective iron-chelating agents must be able to selectively bind and neutralize ferric iron, the oxidized form of non-transferrin bound iron which likely accounts for most iron toxicity through catalytic production of hydroxyl radicals and oxidation products (Esposito et al, 2003, Blood 102:2670-2677). These agents are structurally diverse, but all possess oxygen or nitrogen donor atoms able to form neutralizing octahedral coordination complexes with individual iron atoms in stoichiometries of 1:1 (hexadentate agents), 2:1 (tridentate), or 3:1 (bidentate) (Kalinowski et al, 2005, Pharmacol Rev 57:547-583). Effective iron-chelating agents also are relatively low molecular weight (less than 700 daltons), with solubility in both water and lipid to enable access to affected tissues. Specific examples of iron-chelating molecules are deferoxamine, a hexadentate agent of bacterial origin requiring daily parenteral administration, and the orally active synthetic agents deferiprone (bidentate) and deferasirox (tridentate). Combination therapy consisting of same-day administration of two iron-chelating agents shows promise in patients unresponsive to chelation monotherapy and also in overcoming issues of poor patient compliance with dereroxamine alone (Cao et al, 2011, Pediatr Rep 3(2):e17; Galanello et al, 2010, Ann NY Acad Sci 1202:79-86).

In certain embodiments, GDF15 polypeptides may be used in combination with hepcidin agonists for ineffective erythropoiesis. A circulating polypeptide produced mainly in the liver, hepcidin is considered a master regulator of iron metabolism by virtue of its ability to induce the degradation of ferroportin, an iron-export protein localized on absorptive enterocytes, hepatocytes, and macrophages. Broadly speaking, hepcidin reduces availability of extracellular iron, so hepcidin agonists may be beneficial in the treatment of ineffective erythropoiesis (Nemeth, 2010, Adv Hematol 2010:750643). This view is supported by beneficial effects of increased hepcidin expression in a mouse model of β-thalassemia (Gardenghi et al, 2010, J Clin Invest 120: 4466-4477).

In some embodiments, GD15 polypeptides may be used in combination with EPO receptor activators to reduce the required dose of these activators in patients that are susceptible to adverse effects of EPO. The primary adverse effects of EPO are an excessive increase in the hematocrit or hemoglobin levels and polycythemia. Elevated hematocrit levels can lead to hypertension (more particularly aggravation of hypertension) and vascular thrombosis. Other adverse effects of EPO which have been reported, some of which related to hypertension, are headaches, influenza-like syndrome, obstruction of shunts, myocardial infarctions and cerebral convulsions due to thrombosis, hypertensive encephalopathy, and red cell blood cell applasia (Singibarti, (1994) J. Clin Investig 72(suppl 6), S36-S43; Horl et al. (2000) Nephrol Dial Transplant 15(suppl 4), 51-56; Delanty et al. (1997) Neurology 49, 686-689; Bunn (2002) N Engl J Med 346(7), 522-523).

The rapid effect on red blood cell levels of the GDF15 polypeptides disclosed herein indicate that these agents act by a different mechanism than EPO. Accordingly, these antagonists may be useful for increasing red blood cell and hemoglobin levels in patients that do not respond well to EPO. For example, a GDF15 polypeptide may be beneficial for a patient in which administration of a normal to increased (>300 IU/kg/week) dose of EPO does not result in the increase of hemoglobin level up to the target level. Patients with an inadequate EPO response are found for all types of anemia, but higher numbers of non-responders have been observed particularly frequently in patients with cancers and patients with end-stage renal disease. An inadequate response to EPO can be either constitutive (i.e. observed upon the first treatment with EPO) or acquired (e.g. observed upon repeated treatment with EPO).

Numerous genes contribute to classical sickle-cell disease (SCD; drepanocytosis). Primarily, sickle-cell disease is an inherited disorder caused by a mutation in the β-globin gene (a mutation of a glutamate to a valine at codon 6). See, e.g., Kassim et al. (2013) Annu Rev Med, 64: 451-466. Sickle-cell anemia refers to the most common form of sickle-cell disease, with a homozygous mutation in the $\beta^S$ allele (HbSS), affecting 60 to 70% of people with sickle-cell disease. Because of the mutation in the β-globin gene, abnormal hemoglobin molecules are produced with a hydrophobic motif that is exposed when it is in a deoxygenated state [see, e.g., Eaton et al. (1990) Adv Protein Chem, 40: 63-279; Steinberg, MH (1999) N Engl J Med 340(13): 1021-1030; and Ballas et al. (1992) Blood, 79(8): 2154-63]. Once exposed, the chains of the separate hemoglobin molecules polymerize, which results in damage to the red blood cell membrane and cellular dehydration. The membrane damage is manifested, in part, by a redistribution of membrane lipids leading to the expression of phosphatidylserine on the outer leaflet of the erythrocyte membrane [see, e.g., (2002) Blood 99(5): 1564-1571]. Externalized phosphatidylserine promotes adhesion to both macrophages and activated endothelial cells, which contributes to vascular (vaso) occlusion. Thus, at low oxygen states, the red cell's hemoglobin precipitates into long crystals that cause it to elongate, morphologically switching into a "sickled" red blood cell. Both genotype and the extent and degree of deoxygenation contribute to the severity of hemoglobin polymerization. It has been demonstrated that the presence of fetal hemoglobin proportionally reduces the amount of pathological hemoglobin polymers and is protective from vaso-occlusive crises.

In some embodiments, an GDF15 polypeptide can be used treat sickle-cell disease, particularly used to treat or prevent one or more complications of sickle-cell disease (e.g., anemia, anemia crisis, splenomegaly, pain crisis, chest syndrome, acute chest syndrome, blood transfusion requirement, organ damage, pain medicine (management) requirement, splenic sequestration crises, hyperhemolytic crisis, vaso-occlusion, vaso-occlusion crisis, acute myocardial infarction, sickle-cell chronic lung disease, thromboemboli, hepatic failure, hepatomegaly, hepatic sequestration, iron overload, splenic infarction, acute and/or chronic renal failure, pyelonephritis, aneurysm, ischemic stroke, intraparenchymal hemorrhage, subarachnoid hemorrhage, intraventricular hemorrhage, peripheral retinal ischemia, proliferative sickle retinopathy, vitreous hemorrhage, and/or priapism) in a subject in need thereof.

In certain aspects, a GDF15 polypeptide may be administered to a subject in need thereof in combination with one or more additional agents (e.g., hydroxyurea, an EPO antagonist, EPO, an opioid analgesic, a non-steroidal anti-inflammatory drug, a corticosteroid, an iron-chelating agent) or supportive therapies (e.g., red blood cell transfusion) for treating sickle-cell disease or one or more complications of sickle-cell disease.

The mainstay of treatment for the majority of patients with sickle-cell disease is supportive. Current treatment options for patients with sickle-cell disease include antibiotics, pain management, intravenous fluids, blood transfusion, surgery, and compounds such as hydroxyurea.

Hydroxyurea (e.g. Droxia®) is an approved drug for treating sickle-cell disease. Hydroxyurea is an S-phase cytotoxic drug and is used for long-term therapy. It is believed to increase the levels of hemoglobin F which prevents formation of S-polymers and red cell sickling. It is also believed to increase NO production. A multi-center trial of hydroxyurea in adults with sickle-cell disease showed that hydroxyurea reduced the incidence of painful episodes by nearly half. However, presently hydroxyurea is used only in patients who suffer severe complications of sickle-cell disease and who are capable of following the daily dosage regimes. The general belief is that hydroxyurea therapy is effective only if given in a structured environment with a high potential for compliance. Unfortunately, many patients with sickle-cell disease are refractory to hydroxyurea. In some embodiments, the methods of the present disclosure relate to treating sickle-cell disease in a subject in need thereof by administering a combination of an GDF15 polypeptide of the disclosure and hydroxyurea. In some embodiments, the methods of the present disclosure relate to treating or preventing one or more complications of sickle-cell disease in a subject in need thereof by administering a combination of a GDF15 polypeptide of the disclosure and hydroxyurea.

In certain embodiments, a GDF15 polypeptide the disclosure, optionally combined with an EPO receptor activator and/or one or more additional therapies (e.g., treatment with hydroxyurea), may be used in combination with transfusion of either red blood cells or whole blood to treat anemia in patients with sickle-cell disease or one or more complications of sickle-cell disease. In patients who receive frequent transfusions of whole blood or red blood cells, normal mechanisms of iron homeostasis can be overwhelmed, eventually leading to toxic and potentially fatal accumulation of iron in vital tissues such as heart, liver, and endocrine glands. Regular red blood cell transfusions require exposure to various donor units of blood and hence a higher risk of alloimmunization. Difficulties with vascular access, availability of and compliance with iron chelation, and high cost are some of the reasons why it can be beneficial to limit the number of red blood cell transfusions]. In some embodiments, the methods of the present disclosure relate to treating sickle-cell disease in a subject in need thereof by administering a combination of a GDF15 polypeptide and one or more blood cell transfusions. In some embodiments, the methods of the present disclosure relate to treating or preventing one or more complications of sickle-cell disease in a subject in need thereof by administering a combination of a GDF15 antagonist of the disclosure and one or more red blood cell transfusions. In some embodiments, treatment with a GDF15 polypeptide is effective at decreasing the transfusion requirement in a patient with sickle-cell disease, e.g., reduces the frequency and/or amount of blood transfusion required to effectively treat sickle-cell disease or one or more complications of sickle-cell disease.

In certain embodiments, a GDF15 polypeptide, optionally combined with an EPO receptor activator and/or one or more additional therapies (e.g., treatment with hydroxyurea), may be used in combination with one or more iron-chelating molecules to promote iron excretion in the urine and/or stool and thereby prevent or reverse tissue iron overload in SCD patients. Effective iron-chelating agents should be able to selectively bind and neutralize ferric iron, the oxidized form of non-transferrin bound iron which likely accounts for most iron toxicity through catalytic production of hydroxyl radicals and oxidation products [see, e.g., Esposito et al. (2003) Blood 102:2670-2677]. These agents are structurally diverse, but all possess oxygen or nitrogen donor atoms able to form neutralizing octahedral coordination complexes with individual iron atoms in stoichiometries of 1:1 (hexadentate agents), 2:1 (tridentate), or 3:1 (bidentate) [Kalinowski et al. (2005) Pharmacol Rev 57:547-583]. In general, effective iron-chelating agents also are relatively low molecular weight (e.g., less than 700 daltons), with solubility in both water and lipids to enable access to affected tissues. Specific examples of iron-chelating molecules include deferoxamine (also known as desferrioxamine B, desferoxamine B, DFO-B, DFOA, DFB, or desferal), a hexadentate agent of bacterial origin requiring daily parenteral administration, and the orally active synthetic agents deferiprone (bidentate; also known as Ferriprox™) and deferasirox (tridentate; also known as bis-hydroxyphenyl-triazole, ICL670, or Exjade™). Combination therapy consisting of same-day administration of two iron-chelating agents shows promise in patients unresponsive to chelation monotherapy and also in overcoming issues of poor patient compliance with dereroxamine alone [Cao et al. (2011) Pediatr Rep 3(2):e17; and Galanello et al. (2010) Ann NY Acad Sci 1202:79-86].

In certain aspects, the disclosure provides methods of treating MDS and sideroblastic anemias, particularly treating or preventing one or more subtypes or complications of MDS, with a GDF15 polypeptide, including the treatment of patients with MDS characterized by the presence of ring sideroblasts and/or one or more mutations in the gene SF3B1. In particular, the disclosure provides methods for using a GDF15 polypeptide to treat or prevent one or more complications of MDS and sideroblastic anemias including, for example, anemia, neutropenia, splenomegaly, blood transfusion requirement, development of acute myeloid leukemia, iron overload, and complications of iron overload, among which are congestive heart failure, cardiac arrhythmia, myocardial infarction, other forms of cardiac disease, diabetes mellitus, dyspnea, hepatic disease, and adverse effects of iron chelation therapy.

In particular, the disclosure provides methods for using a GDF15 polypeptide to treat or prevent anemia or other complications in a subtype of MDS, including MDS patients with elevated numbers of erythroblasts (hypercellularity) in bone marrow; in MDS patients with more than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, or 95% sideroblasts in bone marrow; in MDS patients with refractory anemia with ring sideroblasts (RARS); in MDS patients with refractory anemia with ring sideroblasts and thrombocytosis (RARS-T); in MDS patients with refractory cytopenia with unilineage dysplasia (RCUD); in MDS patients with refractory cytopenia with multilineage dysplasia and ring sideroblasts (RCMD-RS); in MDS patients with a somatic mutation in SF3B1, SRSF2, DNMT3A, or TET2; in MDS patients without a somatic mutation in ASXL1 or ZRSR2; in MDS patients with iron overload; and in MDS patients with neutropenia.

Also in particular, the disclosure provides methods for using a GDF15 polypeptide, to treat or prevent anemia or other complications of a sideroblastic anemia, including but not limited to refractory anemia with ring sideroblasts (RARS); refractory anemia with ring sideroblasts and thrombocytosis (RARS-T); refractory cytopenia with multilineage dysplasia and ring sideroblasts (RCMD-RS); sideroblastic anemia associated with alcoholism; drug-induced sideroblastic anemia; sideroblastic anemia resulting from copper deficiency (zinc toxicity); sideroblastic anemia resulting from hypothermia; X-linked sideroblastic anemia (XLSA); SLC25A38 deficiency; glutaredoxin 5 deficiency; erythropoietic protoporphyria; X-linked sideroblastic anemia with ataxia (XLSA/A); sideroblastic anemia with B-cell immunodeficiency, fevers, and developmental delay (SIFD); Pearson marrow-pancreas syndrome; myopathy, lactic acidosis, and sideroblastic anemia (MLASA); thiamine-responsive megaloblastic anemia (TRIVIA); and syndromic/non-syndromic sideroblastic anemia of unknown cause.

In certain aspects the disclosure provides methods for treating or preventing disorders or complications of a disorder that is associated with germ line or somatic mutations in SF3B1, such as myelodysplastic syndrome, chronic lymphocytic leukemia (CLL), and acute myeloid leukemia (AML) as well as in breast cancer, pancreatic cancer, gastric cancer, prostate cancer, and uveal melanoma. In certain aspects the disorder may be in a subject that has bone marrow cells that test positive for an SF3B1 mutation, particularly myelodysplastic syndrome, CLL and AML. Optionally a mutation in the SF3B1 gene is in an exon, intron or 5' or 3' untranslated region. Optionally a mutation in SF3B1 causes a change in the amino acid sequence or does not cause a change in the amino acid sequence of the protein encoded by the gene. Optionally a mutation in the SF3B1 gene causes a change in the amino acid of the protein encoded by the gene selected from the following changes: K182E, E491G, R590K, E592K, R625C, R625G, N626D, N626S, H662Y, T663A, K666M, K666Q, K666R, Q670E, G676D, V701I, I704N, I704V, G740R, A744P, D781G, A1188V, N619K, N626H, N626Y, R630S, I704T, G740E, K741N, G742D, D894G, Q903R, R1041H, I1241T, G347V, E622D, Y623C, R625H, R625L, H662D, H662Q, T663I, K666E, K666N, K666T, K700E, and V701F.

Patients may be treated with a dosing regimen intended to restore the patient to a target hemoglobin level, usually between about 10 g/dl and about 12.5 g/dl, and typically about 11.0 g/dl (see also Jacobs et al., 2000, Nephrol Dial Transplant 15, 15-19), although lower target levels may cause fewer cardiovascular side effects. Alternatively, hematocrit levels (percentage of the volume of a blood sample occupied by the cells) can be used as a measure for the condition of red blood cells. Hematocrit levels for healthy individuals range from 41 to 51% for adult males and from 35 to 45% for adult females. Target hematocrit levels are usually around 30-33%. Moreover, hemoglobin/hematocrit levels vary from person to person. Thus, optimally, the target hemoglobin/hematocrit level can be individualized for each patient.

In certain embodiments, the present invention provides methods for managing a patient that has been treated with, or is a candidate to be treated with, a GDF15 polypeptide by measuring one or more hematologic parameters in the patient. The hematologic parameters may be used to evaluate appropriate dosing for a patient who is a candidate to be treated with a GDF15 polypeptide, to monitor the hematologic parameters during treatment with a GDF15 polypeptide, to evaluate whether to adjust the dosage during treatment with a GDF15 polypeptide, and/or to evaluate an appropriate maintenance dose of a GDF15 polypeptide. If one or more of the hematologic parameters are outside the normal level, dosing with a GDF15 polypeptide may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art-recognized methods. Such parameters may be determined using a blood sample from a patient. Increases in red blood cell levels, hemoglobin levels, and/or hematocrit levels may cause increases in blood pressure.

In one embodiment, if one or more hematologic parameters are outside the normal range, or on the high side of normal, in a patient who is a candidate to be treated with a GDF15 polypeptide, then onset of administration of the GDF15 polypeptide may be delayed until the hematologic parameters have returned to a normal or acceptable level either naturally or via therapeutic intervention. For example, if a candidate patient is hypertensive or prehypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels, then administration of the GDF15 polypeptide may be delayed until the levels have returned to a normal or acceptable level.

In certain embodiments, if one or more hematologic parameters are outside the normal range, or on the high side of normal, in a patient who is a candidate to be treated with a GDF15 polypeptide, then the onset of administration may be delayed. However, the dosage amount or frequency of dosing of the GDF15 polypeptide may be set at an amount that would reduce the risk of an unacceptable increase in the hematologic parameters arising upon administration of the GDF15 polypeptide. Alternatively, a therapeutic regimen may be developed for the patient that combines a GDF15 polypeptide with a therapeutic agent that addresses the undesirable level of the hematologic parameter. For example, if the patient has elevated blood pressure, or the GDF15 polypeptide appears to be causing elevated blood pressure, then a therapeutic regimen involving administration of a GDF15 polypeptide and a blood pressure lowering agent may be designed. For a patient having lower than desired iron stores, a therapeutic regimen of a GDF15 polypeptide and iron supplementation may be developed.

In one embodiment, baseline parameter(s) for one or more hematologic parameters may be established for a patient who is a candidate to be treated with a GDF15 polypeptide and an appropriate dosing regimen established for that patient based on the baseline value(s). Alternatively, established baseline parameters based on a patient's medical history could be used to inform an appropriate dosing regimen of GDF15 polypeptide for a patient. For example, if a healthy patient has an established baseline blood pressure reading that is above the defined normal range it may not be necessary to bring the patient's blood pressure into the range that is considered normal for the general population prior to treatment with the GDF15 polypeptide. A patient's baseline values for one or more hematologic parameters prior to treatment with a GDF15 polypeptide may also be used as the relevant comparative values for monitoring any changes to the hematologic parameters during treatment with the GDF15 polypeptide.

In certain embodiments, one or more hematologic parameters are measured in patients who are being treated with a GDF15 polypeptide. The hematologic parameters may be used to monitor the patient during treatment and permit adjustment or termination of the dosing with the GDF15 polypeptide or additional dosing with another therapeutic agent. For example, if administration of a GDF15 polypeptide results in an increase in blood pressure, red blood cell level, or hemoglobin level, or a reduction in iron stores, then the dose of the GDF15 polypeptide may be reduced in amount or frequency in order to decrease the effects of the GDF15 polypeptide on the one or more hematologic parameters. If administration or a GDF15 polypeptide results in a change in one or more hematologic parameters that is adverse to the patient, then the dosing of the GDF15 polypeptide may be terminated either temporarily, until the hematologic parameter(s) return to an acceptable level, or permanently. Similarly, if one or more hematologic parameters are not brought within an acceptable range after reducing the dose or frequency of administration of the GDF15 polypeptide then the dosing may be terminated. As an alternative, or in addition to, reducing or terminating the dosing with the GDF15 polypeptide, the patient may be dosed with an additional therapeutic agent that addresses the undesirable level in the hematologic parameter(s), such as, for example, a blood pressure lowering agent or an iron supplement. For example, if a patient being treated with a GDF15 polypeptide has elevated blood pressure, then dosing with the GDF15 polypeptide may continue at the same level, and a blood pressure-lowering agent may be added to the treatment regimen; dosing with the GDF15 polypeptide may be reduced (e.g., in amount and/or frequency), and a blood pressure-lowering agent may be added to the treatment regimen; or dosing with the GDF15 polypeptide may be terminated, and the patient may be treated with a blood pressure-lowering agent.

4. Pharmaceutical Preparations

In certain embodiments, GDF15 polypeptides of the present invention are formulated with a pharmaceutically acceptable carrier. For example, a GDF15 polypeptide can be administered alone or as a component of a pharmaceutical preparation. The subject compounds may be formulated for administration in any convenient way for use in human or veterinary medicine. As noted above, it may be desirable to prepare a GDF15 polypeptide in a formulation comprising a prodomain polypeptide.

In certain embodiments, the therapeutic method of the invention includes administering the preparation systemically, or locally as an implant or device. When administered, the pharmaceutical preparation for use in this invention is, of course, in a pyrogen-free, physiologically acceptable form. Therapeutically useful agents other than the GDF15 polypeptides which may also optionally be included in the preparation as described above, may be administered simultaneously or sequentially with the subject GDF15 polypeptides.

Typically, compounds will be administered parenterally. Pharmaceutical preparations suitable for parenteral administration may comprise one or more GDF15 polypeptides in combination with one or more pharmaceutically acceptable sterile isotonic aqueous or nonaqueous solutions, dispersions, suspensions or emulsions, or sterile powders (e.g., lyophilates) which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, sugars, ethanol, polyols (such as glycerol, propylene glycol, polyethylene glycol, and the like), and suitable mixtures thereof, vegetable oils, such as olive oil, and injectable organic esters, such as ethyl oleate.

Further, the preparation may be encapsulated or injected in a form for delivery to a target tissue site. In certain embodiments, preparations of the present invention may include a matrix capable of delivering one or more therapeutic compounds (e.g., GDF15 polypeptides) to a target tissue site, providing a structure for the developing tissue and optimally capable of being resorbed into the body. For example, the matrix may provide slow release of the GDF15 polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

It is understood that the dosage regimen will be determined by the attending physician considering various factors which modify the action of the GDF15 polypeptides. The various factors include, but are not limited to, the patient's red blood cell count, hemoglobin level, systolic or diastolic blood pressure or other diagnostic assessments, the desired target red blood cell count, the patient's age, sex, and diet, the severity of any disease that may be contributing to a depressed red blood cell level, time of administration, and other clinical factors. The addition of other known growth factors to the final composition may also affect the dosage. Progress can be monitored by periodic assessment of red blood cell and hemoglobin levels, as well as assessments of reticulocyte levels and other indicators of the hematopoietic process.

In certain embodiments, the present invention also provides gene therapy for the in vivo production of GDF15 polypeptides. Such therapy would achieve its therapeutic effect by introduction of the GDF15 polynucleotide sequences into cells or tissues having the disorders as listed above. Delivery of GDF15 polynucleotide sequences can be achieved using a recombinant expression vector such as a chimeric virus or a colloidal dispersion system. Preferred for therapeutic delivery of GDF15 polynucleotide sequences is the use of targeted liposomes.

Various viral vectors which can be utilized for gene therapy as taught herein include adenovirus, herpes virus, vaccinia, or an RNA virus such as a retrovirus. The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the GDF15 polynucleotide.

EXEMPLIFICATION

The invention now being generally described, it will be more readily understood by reference to the following examples, which are included merely for purposes of illustration of certain embodiments and embodiments of the present invention, and are not intended to limit the invention.

Example 1

Generation of a Bioactive GDF15 Polypeptide

Applicants previously disclosed methodology for generating native recombinant GDF15 that is bioactive and have used this protein to identify the type I and type II receptors through which GDF15 signals (U.S. patent application Ser. No. 14/465,182).

Stable Expression of GDF15 in CHO Cells

Applicants used CHO cells to express mature human GDF15 (hGDF15) and murine GDF15 (mGDF15) for further studies. UCOE™-based constructs encoding human GDF15 precursor protein (SEQ ID NO: 13) or murine GDF15 precursor protein (SEQ ID NO: 14) were stably transfected into a CHO-PACE cell line. Clones were selected in methotrexate levels of 10 nM, 20 nM, and 50 nM, and any clones that formed colonies (one or two per methotrexate concentration) were then pooled. No gene amplification was performed since it is difficult to amplify UCOE™ pools while maintaining stability of expression. Instead of dilution cloning, high-expressing pools were identified and used for generating hGDF15 and mGDF15.

Purification of Human GDF15

To begin purification, conditioned media from CHO cells stably expressing hGDF15 was adjusted to pH 4.7 with acetic acid. After incubation of media for 10 min at ambient temperature, precipitate was removed by centrifugation. Supernatant was filtered with a 0.8 µm disposable filter. An SP Sepharose™ Fast Flow column (GE Healthcare) was equilibrated with buffers A (20 mM sodium acetate, pH 4.7) and B (20 mM sodium acetate, 1 M NaCl, pH 4.7). Loading was performed at 100 cm/hr. The column was washed with 20% B (200 mM NaCl) until no more protein eluted from the column and then washed back to 0% B to remove any residual salt. Protein was eluted with 50 mM Tris, 6 M urea, pH 8.0 (Tris-urea pool) until no more protein eluted from the column, followed by elution with 50 mM Tris, 6 M urea, 1 M NaCl, pH 8.0 (Tris-urea-salt pool). Each pool was dialyzed in 50 mM 4-morpholineethanesulfonic acid (MES, pH 6.5) overnight at 4° C.

GDF15 found in the Tris-urea-salt pool was degraded based on Western blot analysis, so this pool was discarded. The Tris-urea pool was loaded on a Q Sepharose™ Fast Flow column (GE Healthcare) previously equilibrated with buffers A (50 mM MES, pH 6.5) and B (50 mM MES, 1 M NaCl, pH 6.5). The flow-through was collected, and the column was washed with 10% B (100 mM NaCl), followed by a 10-50% B gradient (100-500 mM NaCl) over five column volumes at 120 cm/hr. After evaluation of the flow-through and wash fractions by Western blot, protein was found mainly in the flow-through. The flow-through was injected on a reverse-phase preparative C4 column (Vydac) attached to a HPLC, with buffers A (water/0.1% TFA) and B (acetonitrile/0.1% TFA). A 25-40% B gradient over 1 h at 4.5 mL/min produced the best resolution. Collected fractions were evaluated by SDS-PAGE gel (Sypro Ruby) and Western blot to select those for concentration in a centrifugal evaporator.

Purification of Murine GDF15

The conditioned media was adjusted to pH 4.7 with acetic acid. After incubation of media for 10 min at ambient temperature, precipitate was removed by centrifugation. Supernatant was filtered with a 0.8 µm disposable filter. An SP Sepharose™ Fast Flow column (GE Healthcare) was equilibrated with buffer A (20 mM sodium acetate, pH 4.7) and buffer B (20 mM sodium acetate, 1 M NaCl, pH 4.7). Loading was performed at 100-150 cm/hr, and the column was washed with buffer A until no more protein eluted from the column. The column was washed with 50 mM MES, pH 6.0, until no more protein eluted from the column based on the UV trace. The protein was then eluted with 50 mM MES, 600 mM NaCl, pH 6.0, for 5-6 column volumes. The column was washed with 50 mM MES, 1 M NaCl, pH 6.0, and then with 50 mM Tris, 1 M NaCl, pH 8.0. Although some protein was found in the Tris-eluted fractions by Western blot, previous experiments have indicated that mGDF15 found in these fractions is essentially inactive, so it was not used for further purification. Instead, purification was continued using protein eluted with 600 mM NaCl, pH 6.0. This pool was injected on a reverse-phase preparative C4 column (Vydac) attached to an HPLC. Buffer A was water/0.1% TFA and buffer B was acetonitrile/0.1% TFA. Protein was eluted with a 25-40% B gradient over 1 h at 4.5 mL/min. After evaluation of the reverse-phase column fractions by SDS-PAGE gel (Sypro Ruby) and Western blot, the fractions containing pure mGDF15 were pooled and concentrated in a centrifugal evaporator.

Sequence Confirmation and Bioactivity

The identities of purified recombinant GDF15 polypeptides were confirmed by N-terminal sequencing. Mature recombinant mGDF15 can be purified as full-length (SEQ ID NO: 11) and N'Δ4 truncated (SEQ ID NO: 12) forms. Mature recombinant hGDF15 has been purified in a full-length form (SEQ ID NO: 3) as well as an N'Δ2 truncated form (SEQ ID NO: 4), and Applicants envision N'Δ4 truncated forms of hGDF15 (e.g., SEQ ID NO: 8) analogous to those for mGDF15.

Example 2

Effect of Recombinant GDF15 Administration on Red Blood Cell Indices in Wild-Type Mice Circulating levels of GDF15 are strikingly elevated in human anemias characterized by ineffective erythropoiesis, such as in β-thalassemia (Tanno et al., 2007, Nat Med 13:1096-1101). However, the role of endogenous GDF15 in such diseases has remained unclear due to limited availability of bioactive GDF15 for research studies and uncertainty concerning GDF15 signaling pathways. With bioactive native GDF15 generated and purified as described in Example 1, Applicants investigated the effect of GDF15 treatment on red blood cell number, hemoglobin concentration, and hematocrit during conditions of steady-state erythropoiesis in wild-type mice. In this experiment, adult C57BL/6 mice were treated intraperitoneally with recombinant murine GDF15 (0.3 mg/kg) or vehicle (Tris-buffered saline) every other day for 3 weeks, at which time blood samples were taken via tail vein for analysis by complete blood count (CBC). Compared to vehicle, GDF15 treatment at this dose level and frequency caused statistically significant increases of between approximately 6% and 9.5% in red blood cell numbers, hemoglobin concentration, and hematocrit (FIG. 2). There were no substantial effects of GDF15 treatment on white blood cells or other blood parameters, thus providing evidence for a selective effect on cells of the erythroid lineage. These results indicate that sustained administration of recombinant native GDF15 can increase circulating levels of red blood cells in vivo, as measured by erythrocyte count, hemoglobin concentration, and hematocrit.

Example 3

GDF15 Treatment Rapidly Promotes Formation of Red Blood Cells from Erythroid Progenitors Ex Vivo Effects of sustained GDF15 treatment on red blood cell indices as described in Example 2 could theoretically be mediated by factors other than increased formation of red blood cells; for example, by increased longevity of red blood cells already in the circulation or by decreased plasma volume. Applicants therefore investigated whether recombinant native GDF15 can directly increase formation of red blood cells.

Erythroid progenitor cells were isolated from the livers of wild-type mouse embryos (embryonic day 12) obtained from Jackson Labs. Liver tissue was subjected to mechanical trituration, and the resulting cell suspension was passed through a 300 μm mesh. Liver cells were then incubated with a panel of biotinylated antibodies against Ter119, CD3e, CD11b, CD45R, Ly-6C, and Ly-6G (Biotin Mouse Lineage Panel, BD Pharmingen, #559971) to permit selective exclusion of mature erythroid cells (Ter119+) as well as cells of non-erythroid lineages (CD3e+, etc.) with an Easy Sep Cell Isolation kit (Stem Cell Technologies). The remaining early-stage erythroid progenitor cells [mainly those at the colony-forming unit, erythroid (CFU-E) stage] were then cultured in a suboptimal expansion media that permits, but does not promote, differentiation: StemPro34 media (Life Technologies) supplemented with 2 U/ml EPO, 10 ng/ml SCF, 40 ng/ml IGF-1, 200 μg/ml holotransferrin, and 100 μM β-mercaptoethanol.

Figure 3:
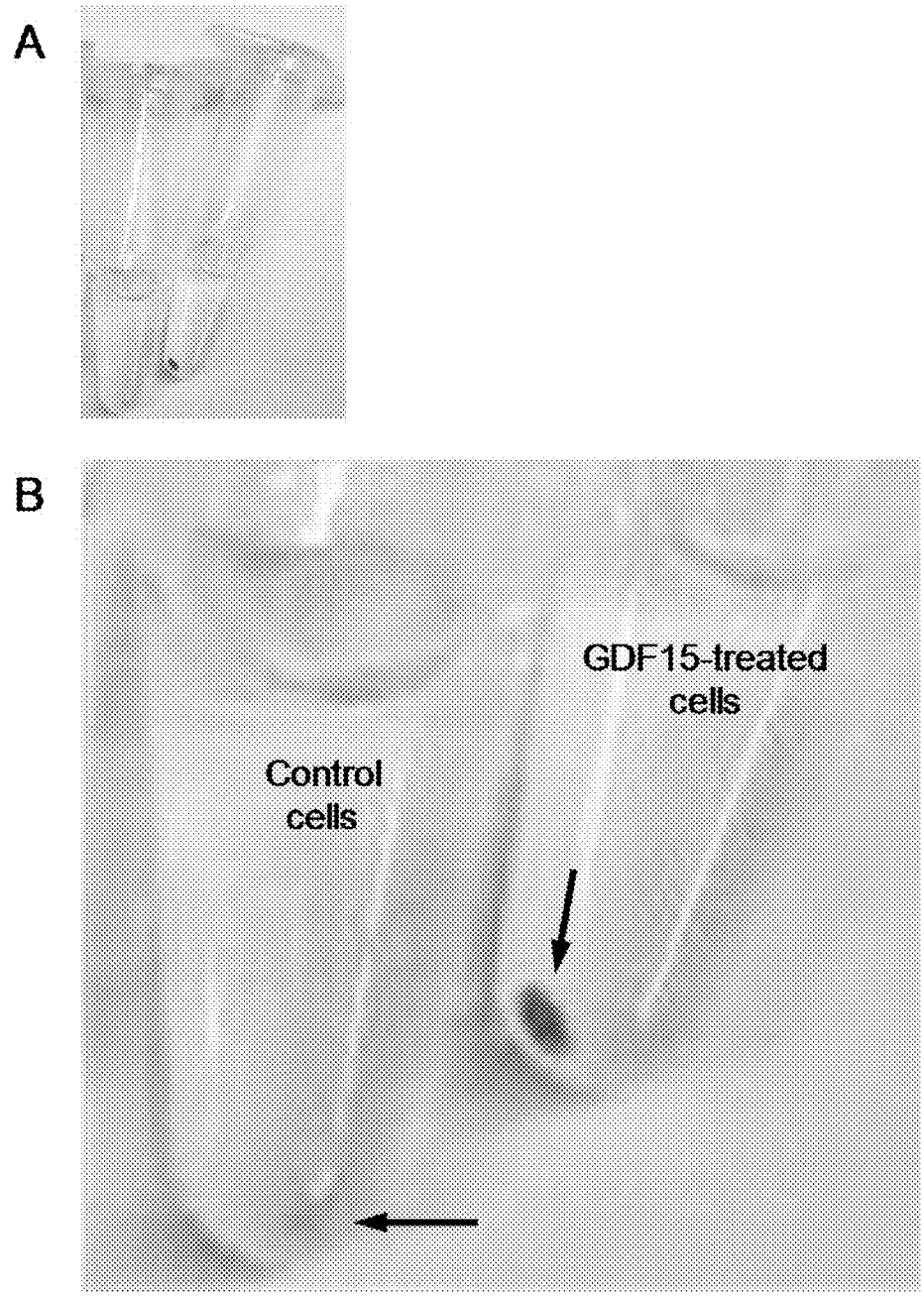
FIG. 3 depicts the ability of GDF15 to rapidly promote formation of red blood cells from erythroid progenitor cells ex vivo. As shown at low (A) and high (B) magnification, erythroid progenitors ($3.2 \times 10^5$ cells) obtained from mouse fetal liver and treated with recombinant murine GDF15 (50 ng/ml) ex vivo for 24 h form a cell pellet whose bright red color (right vial, arrow) contrasts with the pale pellet (left vial, arrow) formed by an equal number of precursors exposed to media alone (control). Intensity of red color corresponds to cellular hemoglobin level, a critical marker of red blood cell maturity.

Purified erythroid progenitors were cultured in this expansion media with or without recombinant murine GDF15. When progenitors treated for 24 h were inspected, it was apparent that those treated with GDF15 (50 ng/ml) formed a cell pellet which was much brighter red than one formed by the same number of progenitor cells exposed to expansion media alone (FIG. 3). The intensity of red color corresponds to cellular hemoglobin level, a functional marker of erythrocyte maturity. Subsequent analysis of these cells by flow cytometry after treatment for 24 or 48 h confirmed that GDF15 significantly increased the number of mature erythroblasts, as determined by increased intensity of Ter119 immunostaining and by reduced cell size (data not shown). It is well-established that as erythroblast differentiation proceeds there is a progressive increase in Ter119 levels and a progressive reduction in erythroblast size. Together, these findings indicate that recombinant GDF15 can rapidly and directly promote formation of red blood cells from erythroid progenitor cells ex vivo.

Example 4

Synergistic Effects of GDF15 and EPO in a Mouse Model of Stress Erythropoiesis

Figure 4:
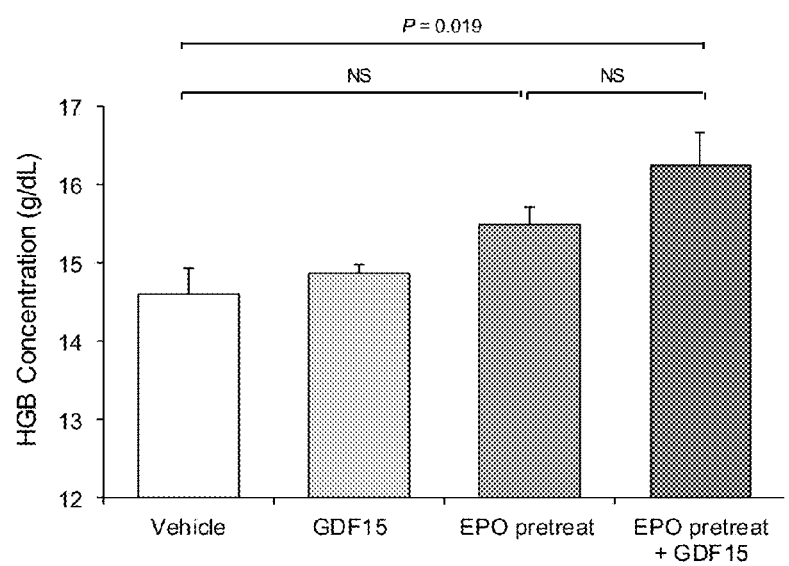
FIG. 4 depicts the rapid synergistic effect of EPO pretreatment and subsequent GDF15 treatment on hemoglobin (Hgb) concentration in a mouse model of stress erythropoiesis. Wild-type mice pretreated with vehicle (TBS) or EPO (1800 U/kg, i.v.) on day 1 to induce stress erythropoiesis were then treated with recombinant murine GDF15 (1 mg/kg, i.v.) or vehicle daily on days 2 and 3, and blood was collected on day 4 for analysis. Combined EPO pretreatment and GDF15 treatment increased hemoglobin concentration by 11% compared to vehicle (P=0.019), a synergistic increase greater than the sum of the separate effects of EPO and GDF15 alone, neither of which were significant. Data are means±SEM; n=5 mice per group; NS, not significant.

Tissue hypoxia resulting from anemia causes activation of a physiologic stress response that increases oxygen delivery to tissues. This response depends on EPO but is thought to differ mechanistically from steady-state erythropoiesis and is therefore termed 'stress erythropoiesis' (Paulson et al., 2011, Curr Opin Hematol 18:139-145). To investigate the effect of GDF15 on red blood cell indices in a mouse model, adult C57BL/6 wild-type mice were pretreated with EPO (1800 U/kg, i.v.) or vehicle (TBS) on day 1 to induce stress erythropoiesis. These mice were then treated with recombinant murine GDF15 (1 mg/kg, i.v.) or vehicle (TBS) daily on days 2 and 3, and blood was collected on day 4 for analysis by complete blood count. In the 3-day time frame of this experiment, neither EPO nor GDF15 alone increased hemoglobin concentration significantly compared to vehicle, whereas combined treatment with the two agents led to a significant increase in hemoglobin concentration which was unexpectedly synergistic; i.e., greater than the sum of their separate effects (FIG. 4). Synergy of this type is generally considered evidence that individual agents are acting through different cellular mechanisms. Notably, treatment of wild-type mice with EPO alone for 24 h caused a transient increase in GDF15 mRNA levels in erythropoietic tissue (bone marrow) of more than 10-fold compared to vehicle (data not shown). Together with other findings (see below), these results suggest that GDF15 is an endogenous mediator of erythropoietic stimulation by EPO, thus providing an underlying basis for the ability of exogenous GDF15 polypeptide to promote red blood cell formation.

Example 5

Endogenous GDF15 Implicated in Recovery from Blood-Loss Anemia in the Mouse

Figure 5:
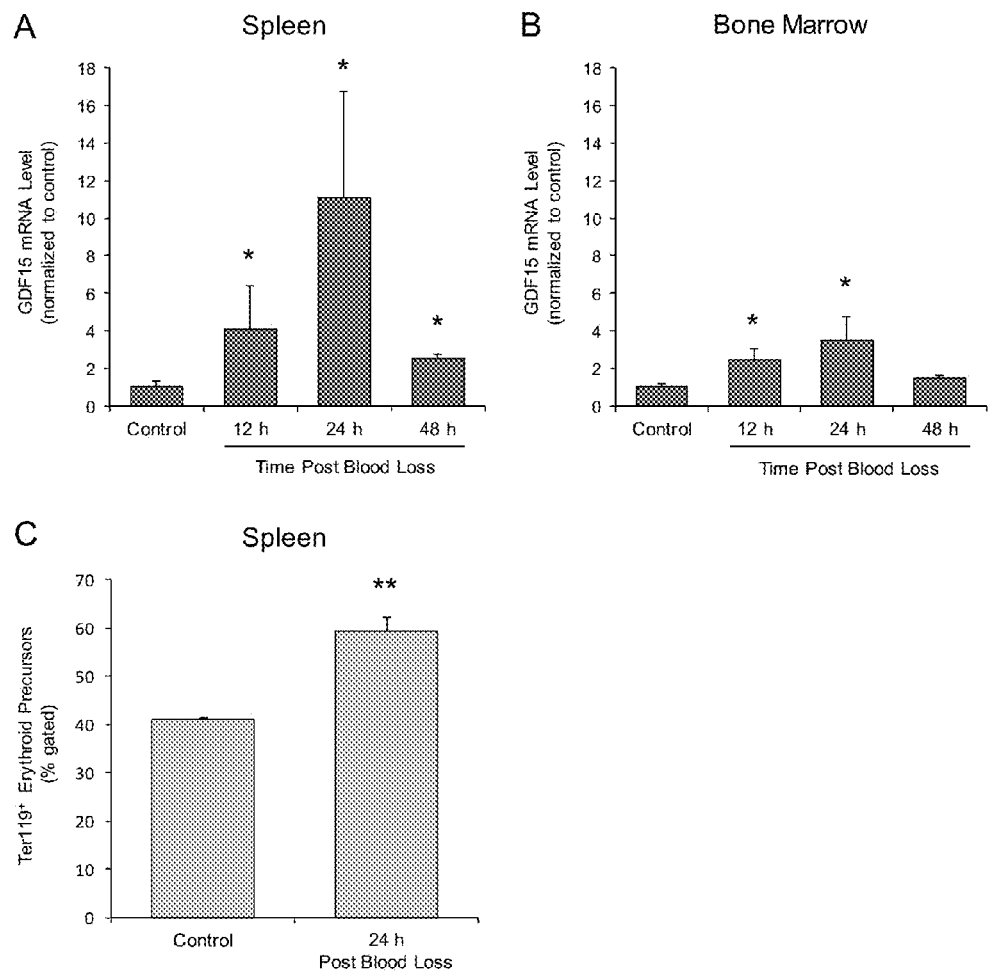
FIG. 5 depicts transient upregulation of GDF15 mRNA in erythroid tissues with a time course similar to accelerated maturation of erythroid precursor cells in a mouse model of blood-loss anemia. Blood removal (phlebotomy) daily for 3 consecutive days in wild-type mice caused GDF15 mRNA levels in spleen (A) and bone marrow (B) to rise significantly by 12 h and to peak 24 h after completion of phlebotomy. (C) By 24 h post completion, blood loss significantly increased the percentage of Ter119$^+$ (late-stage) erythroid precursors in spleen compared to control (unbled mice). Data are means±SEM; n=3-6 mice per group; *, P<0.05; **, P<0.01 vs. control.

Applicants investigated GDF15 expression in erythropoietic tissue under conditions of acute blood-loss anemia, a physiologic form of stress erythropoiesis that does not involve administration of an EPO receptor activator. To induce blood-loss anemia, adult C57BL/6 wild-type mice were phlebotomized (400 μl daily) for three consecutive days accompanied by replacement (i.p.) with an equal volume of saline (Ramos et al., 2011, Blood 117:1379-1389). Bone marrow, spleens, whole blood, and serum were collected upon study termination. RNA was isolated from bone marrow and spleen using a RiboPure Kit from Life Technologies. RT-PCR reactions contained 100 ng of input cDNA generated by an iScript cDNA synthesis kit, and RT-PCR was performed using iTaq Universal Probes Supermix purchased from Bio-Rad. Compared to control (unbled mice), blood removal caused significantly increased levels of GDF15 mRNA at 12 and 24 h (both bone marrow and spleen) and at 48 h (spleen only) after completion of phlebotomy (FIG. 5A-B). These results indicate that GDF15 mRNA levels are transiently upregulated in erythropoietic tissues by blood loss in a physiologically relevant model of stress erythropoiesis.

We next determined whether the foregoing changes in GDF15 expression in phlebotomized mice were accompanied by altered numbers of erythroid precursors in vivo. As determined by flow cytometry performed according to standard methods, there were significantly increased numbers of Ter119+ erythroid precursors in the spleen of mice with blood-loss anemia at 24 h post phlebotomy compared to unbled controls, thus confirming that blood loss triggered a population shift toward more mature cells (FIG. 5C). As expected, spleen weight also more than doubled by 24 h post phlebotomy (data not shown), reflecting increased numbers of erythroid precursors during stress erythropoiesis. These results indicate that a spike in GDF15 mRNA levels occurs in erythroid tissues before and/or during expansion and differentiation of red blood cell precursor populations in response to blood loss in mice. Given the ability of exogenous GDF15 to promote red blood cell formation ex vivo, these results strongly suggest that GDF15 is an inducible erythroid signal promoting formation of red blood cells under hypoxic conditions in vivo.

In summary, the foregoing results indicate that treatment with a GDF15 polypeptide can promote red blood cell formation ex vivo (Example 3) and increase red blood cell indices in vivo under conditions of either steady-state erythropoiesis (Example 2) or stress erythropoiesis (Example 4). In addition, results disclosed here implicate GDF15 as an endogenous erythropoietic signal triggered by acute blood-loss anemia to promote red blood cell production (Example 5). Therefore, a GDF15 polypeptide could be useful for increasing red blood cell numbers, hemoglobin concentrations, and/or hematocrit in patients with various types of anemia and other conditions requiring increased red blood cells and hemoglobin. The effect of combined treatment with a GDF15 polypeptide and an EPO receptor activator can be greater than the sum of the effects of the GDF15 polypeptide and the EPO receptor activator when administered separately at their respective doses. In certain embodiments, this synergism may be advantageous since it enables target levels of red blood cells or hemoglobin concentrations to be attained with lower doses of an EPO receptor activator, thereby avoiding potential adverse effects or other problems associated with higher levels of EPO receptor activation.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A method of treating anemia associated with stress erythropoiesis in a human patient, the method comprising administering to a patient in need thereof an effective amount of a GDF15 polypeptide and an erythropoietin receptor activator, wherein the GDF15 polypeptide comprises an amino acid sequence that is at least 90% identical to the amino acid sequence of SEQ ID NO: 8; wherein the GDF15 polypeptide is capable of binding to ALK5; and wherein the erythropoietin receptor activator is selected from the group consisting of epoetin alfa, epoetin beta, epoetin delta, epoetin omega, darbepoetin alfa and methoxy-polyethylene-glycol epoetin beta.

2. The method of claim 1, wherein the GDF15 polypeptide comprises an amino acid sequence selected from the group consisting of:
   a) a polypeptide comprising an amino acid sequence that is at least 85%, 90%, 91%, 92%, 93%, 94%, 95%, 96%, 97%, 98%, 99%, or 100% identical to the amino acid sequence of SEQ ID NO: 1,
   b) a polypeptide comprising an amino acid sequence that is at least 85%, 90%, 91%, 92%, 93%, 94%, 95%, 96%, 97%, 98%, 99%, or 100% identical to the amino acid sequence of SEQ ID NO: 2,
   c) a polypeptide comprising an amino acid sequence that is at least 85%, 90%, 91%, 92%, 93%, 94%, 95%, 96%, 97%, 98%, 99%, or 100% identical to the amino acid sequence of SEQ ID NO: 3,
   d) a polypeptide comprising an amino acid sequence that is at least 85%, 90%, 91%, 92%, 93%, 94%, 95%, 96%, 97%, 98%, 99%, or 100% identical to the amino acid sequence of SEQ ID NO: 4,
   e) a polypeptide comprising an amino acid sequence that is at least 85%, 90%, 91%, 92%, 93%, 94%, 95%, 96%, 97%, 98%, 99%, or 100% identical to the amino acid sequence of SEQ ID NO: 5,
   f) a polypeptide comprising an amino acid sequence that is at least 85%, 90%, 91%, 92%, 93%, 94%, 95%, 96%, 97%, 98%, 99%, or 100% identical to the amino acid sequence of SEQ ID NO: 6, and
   g) a polypeptide comprising an amino acid sequence that is at least 85%, 90%, 91%, 92%, 93%, 94%, 95%, 96%, 97%, 98%, 99%, or 100% identical to the amino acid sequence of SEQ ID NO: 7.

3. The method of claim 1, wherein the GDF15 polypeptide is administered in a pharmaceutical preparation.

4. The method of claim 3, wherein the pharmaceutical preparation comprises a GDF15 prodomain polypeptide.

5. The method of claim 4, wherein the GDF15 prodomain polypeptide comprises an amino acid sequence that is at least 90%, 91%, 92%, 93%, 94%, 95%, 96%, 97%, 98%, 99%, or 100% identical to the sequence of amino acids 30-196 of SEQ ID NO: 1.

6. The method of claim 4, wherein the pharmaceutical preparation comprises a GDF15 polypeptide noncovalently associated with the GDF15 prodomain polypeptide.

7. The method of claim 1, wherein the GDF15 polypeptide is administered to the patient simultaneously with the erythropoietin receptor activator.

8. The method of claim 1, wherein the GDF15 polypeptide and erythropoietin receptor activator are administered to the patient sequentially.

9. The method of claim 1, wherein the GDF15 polypeptide comprises an amino acid sequence that is at least 95% identical to SEQ ID NO: 8.

10. The method of claim 1, wherein the GDF15 polypeptide comprises the amino acid sequence of SEQ ID NO: 8.

11. The method of claim 1, wherein the stress erythropoiesis is caused by hypoxia.

12. The method of claim 1, wherein the stress erythropoiesis is caused by hemorrhaging.

* * * * *